United States Patent
Xia

(10) Patent No.: US 10,039,736 B1
(45) Date of Patent: Aug. 7, 2018

(54) METHOD FOR TRANSNASAL DELIVERY OF BLOOD-BRAIN BARRIER PERMEATION AGENT AND THERAPEUTIC AGENT

(71) Applicant: Tian Xia, Chicago, IL (US)

(72) Inventor: Tian Xia, Chicago, IL (US)

( * ) Notice: Subject to any disclaimer, the term of this patent is extended or adjusted under 35 U.S.C. 154(b) by 0 days.

(21) Appl. No.: 15/296,069

(22) Filed: Oct. 18, 2016

Related U.S. Application Data

(60) Provisional application No. 62/243,477, filed on Oct. 19, 2015.

(51) Int. Cl.
| | | |
|---|---|---|
| *A61K 31/27* | (2006.01) | |
| *A61K 45/06* | (2006.01) | |
| *A61M 11/06* | (2006.01) | |
| *A61K 9/00* | (2006.01) | |

(52) U.S. Cl.
CPC ............ *A61K 31/27* (2013.01); *A61K 9/0043* (2013.01); *A61K 45/06* (2013.01); *A61M 11/06* (2013.01); *A61M 2210/0618* (2013.01)

(58) Field of Classification Search
CPC ...... A61K 31/27; A61K 9/0043; A61K 45/06; A61M 11/06; A61M 2210/0618
USPC .......................................................... 514/479
See application file for complete search history.

(56) References Cited

U.S. PATENT DOCUMENTS

| | | | |
|---|---|---|---|
| 6,853,858 B2 * | 2/2005 | Shalev | A61M 5/14276 604/20 |
| 7,120,489 B2 | 10/2006 | Gross | |
| 7,190,998 B2 | 3/2007 | Gross | |
| 7,729,759 B2 | 6/2010 | Gross | |
| 9,233,245 B2 | 1/2016 | Dayan | |
| 2004/0210269 A1 | 10/2004 | Gross | |
| 2006/0276854 A1 | 12/2006 | Shalev | |
| 2009/0105783 A1 | 4/2009 | Solberg | |
| 2009/0210026 A1 | 8/2009 | Dayan | |
| 2011/0160623 A1 | 6/2011 | Shalev | |
| 2011/0184494 A1 | 7/2011 | Shalev | |
| 2011/0190668 A1 | 8/2011 | Mishelevich | |

FOREIGN PATENT DOCUMENTS

| | | |
|---|---|---|
| WO | 2001085094 A2 | 11/2001 |
| WO | 2004010923 A2 | 2/2004 |

OTHER PUBLICATIONS

Bar-Shir et al., "Late Stimulation of the Sphenopalatine-Ganglion in Ischemic Rats: Improvement in N-Acetyl-Aspartate Levels and Diffusion Weighted Imaging Characteristics as Seen by MR," J. Magnetic Resonance Imaging 31:1355-1363 (2010).
Khurana et al., "Implant for augmentation of cerebral blood flow trial 1: a pilot study evaluating the safety and effectiveness of the Ischaemic Stroke System for treatment of acute ischaemic stroke" Int. J. Stroke 4:480-485 (2009).
Yarnitsky et al., "Increased BBB permeability by parasympathetic sphenopalatine ganglion stimulation in dogs," Brain Res. 1018(2):236-40 (2004).
Yarnitsky et al., "Blood—brain barrier opened by stimulation of the parasympathetic sphenopalatine ganglion: a new method for macromolecule delivery to the brain," J. Neurosurg 101:303-309 (2004).
Yarnitsky et al., "Reversal of cerebral vasospasm by sphenopalatine ganglion stimulation in a dog model of subarachnoid hemorrhage," Surgical Neurology 64:5-11 (2005).

* cited by examiner

*Primary Examiner* — Kristin A Vajda
(74) *Attorney, Agent, or Firm* — Brinks Gilson & Lione

(57) ABSTRACT

Described herein is a method for treating a central nervous system disorder, said method comprising steps of first transnasally administering to or immediately adjacent the sphenopalatine ganglion a first pharmaceutical agent that effectively enhances permeability of the blood-brain barrier; and thereafter administering a second pharmaceutical agent with known efficacious value for action upon central nervous system tissue. The central nervous system disorder may be related directly to the brain or to other central nervous system tissues and cells.

27 Claims, 16 Drawing Sheets

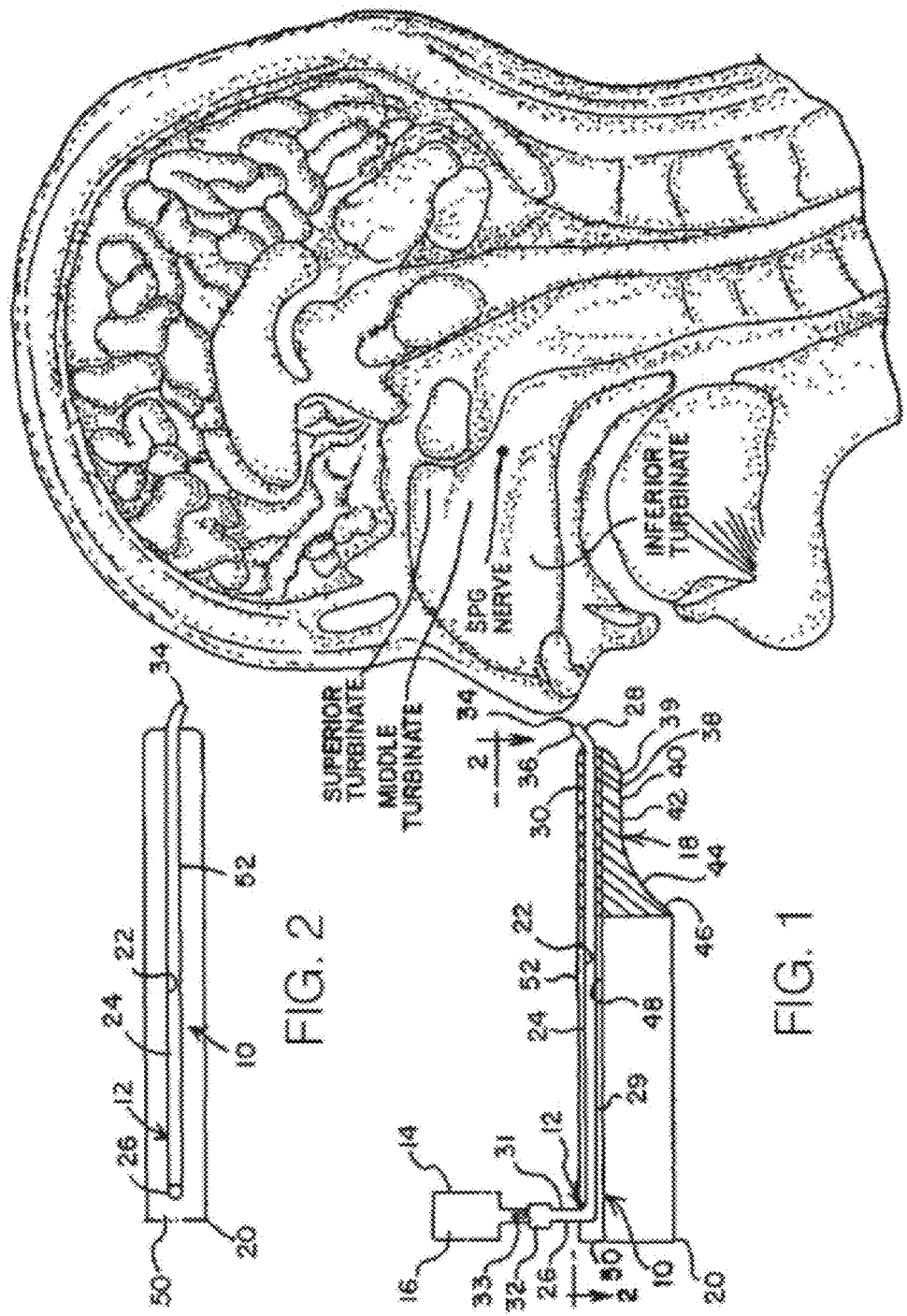

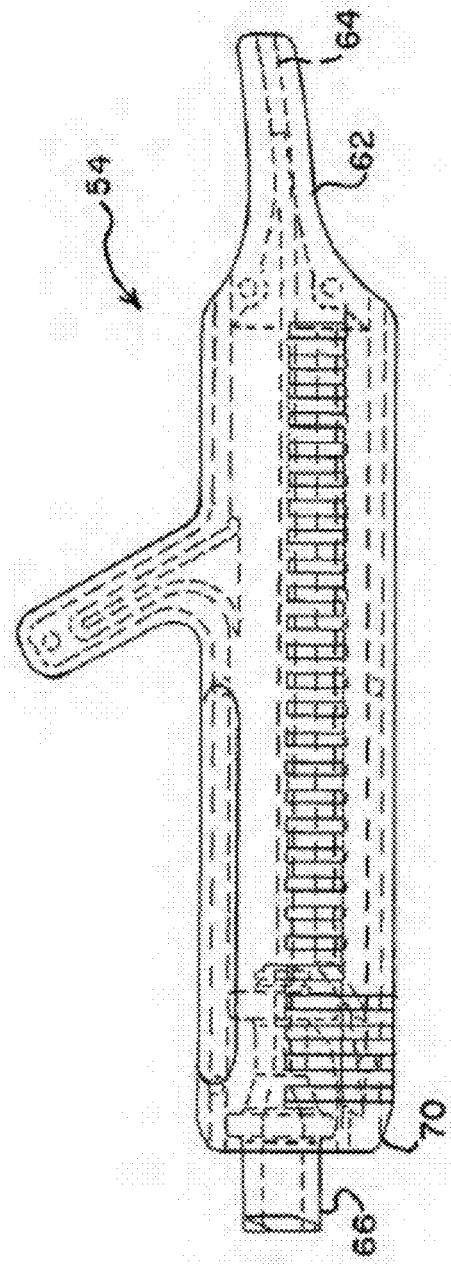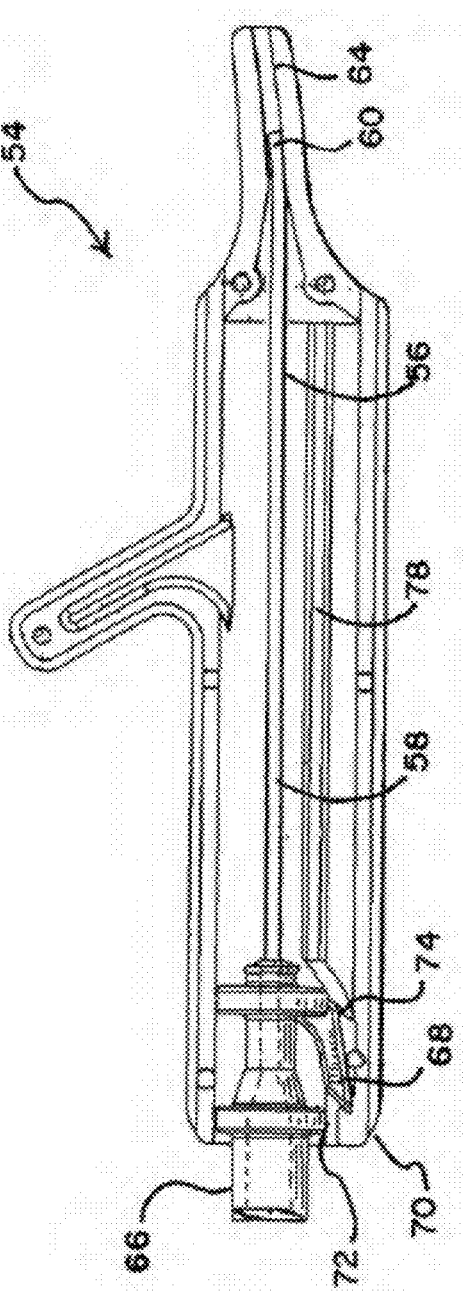

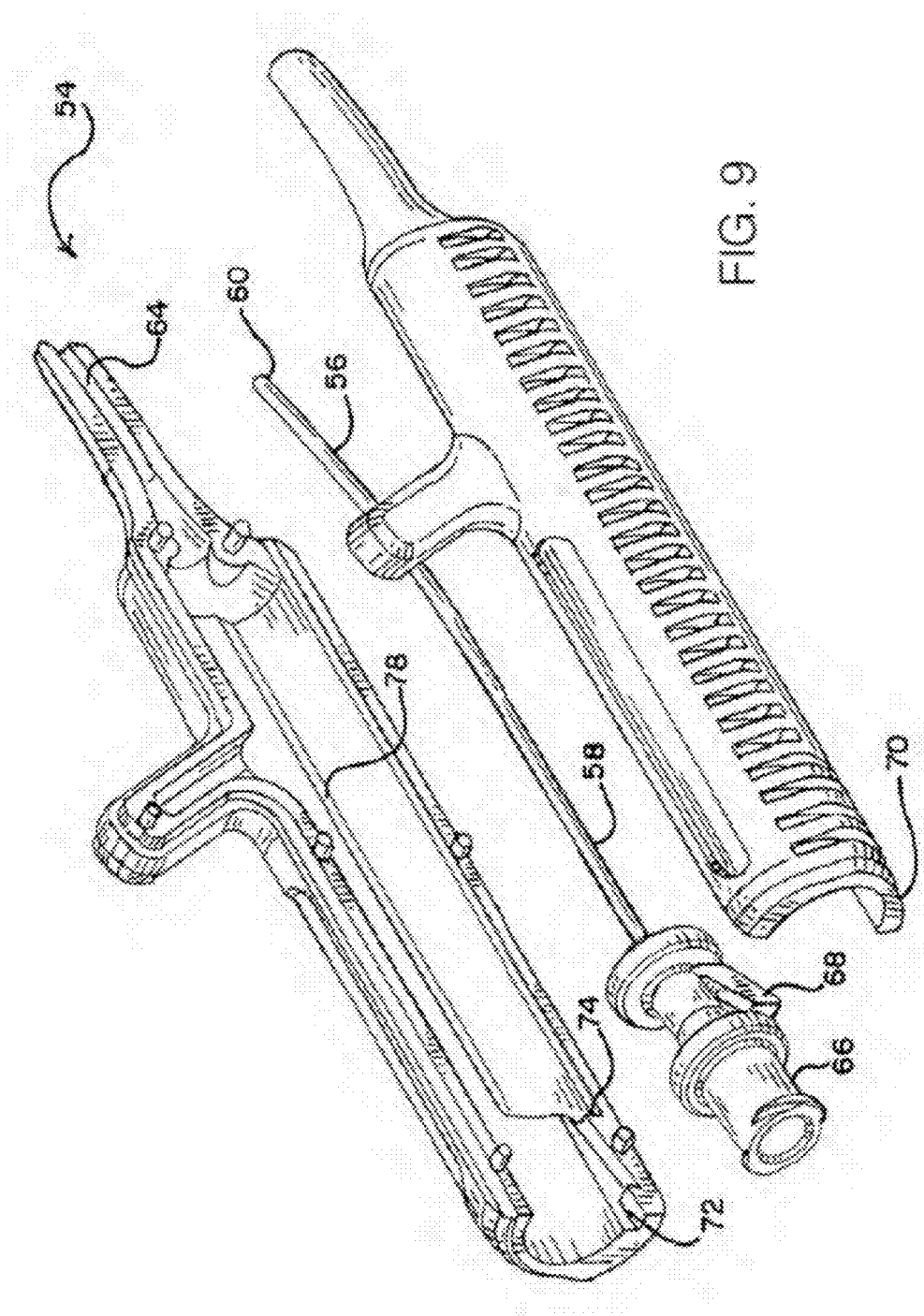

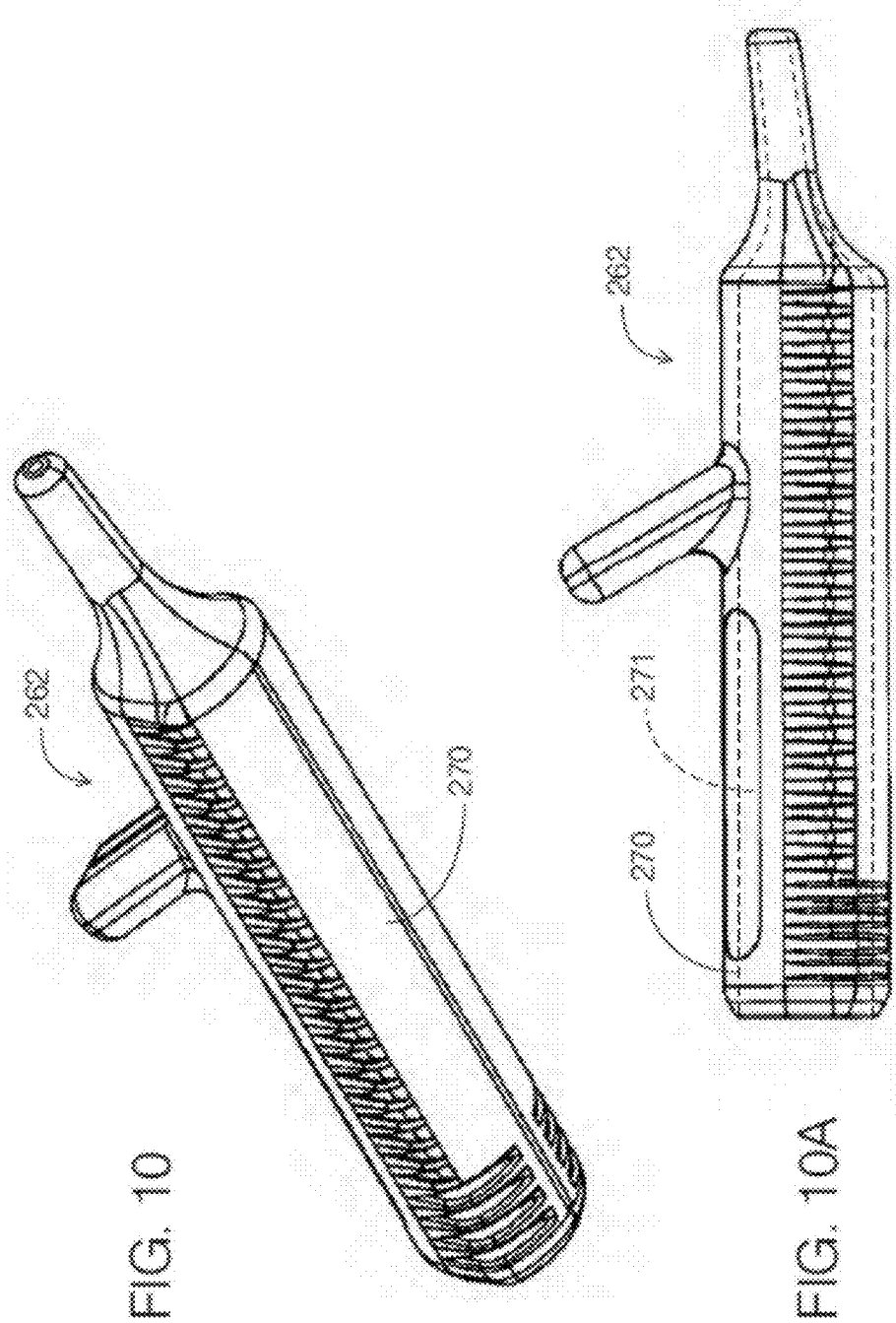

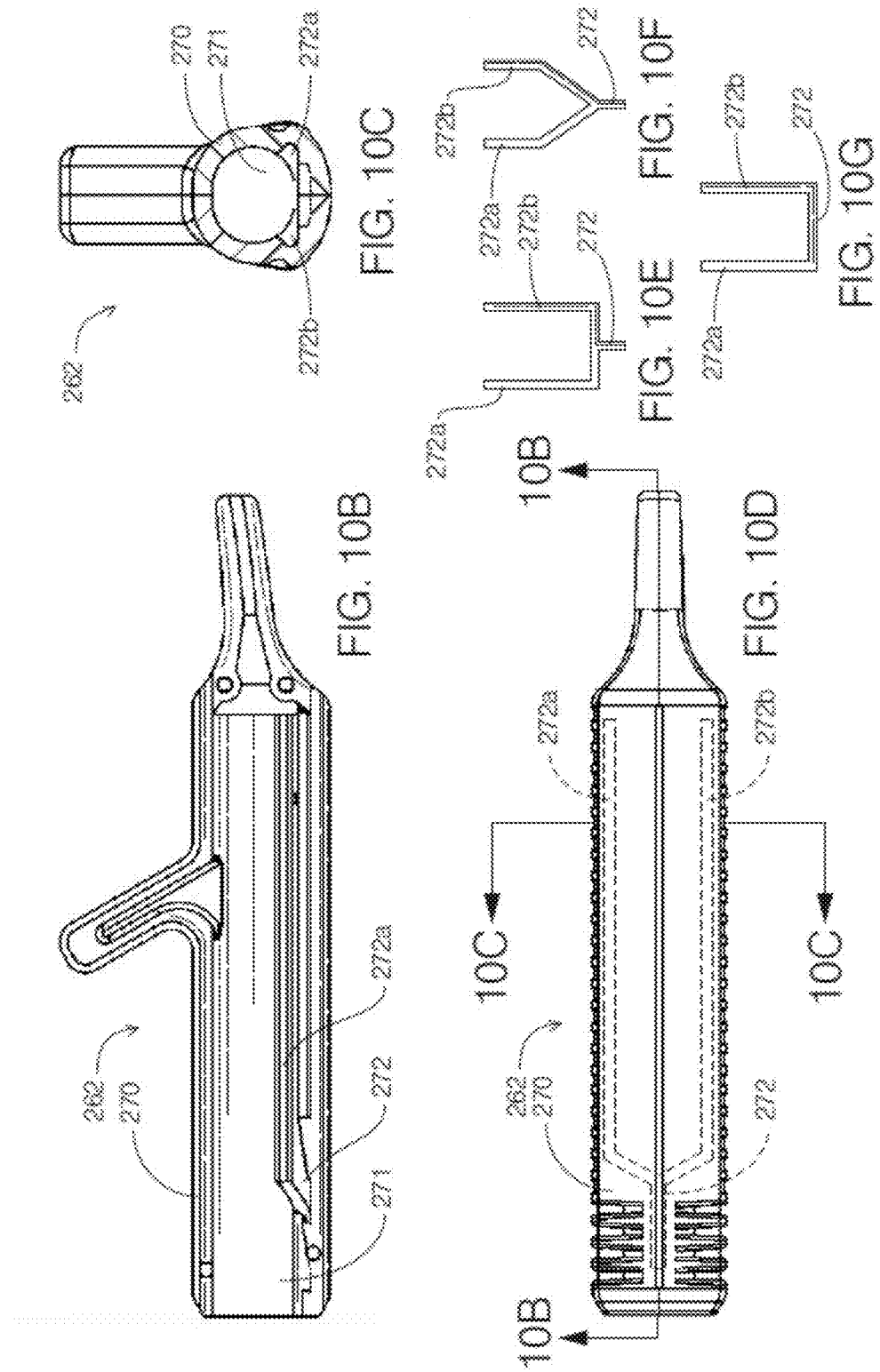

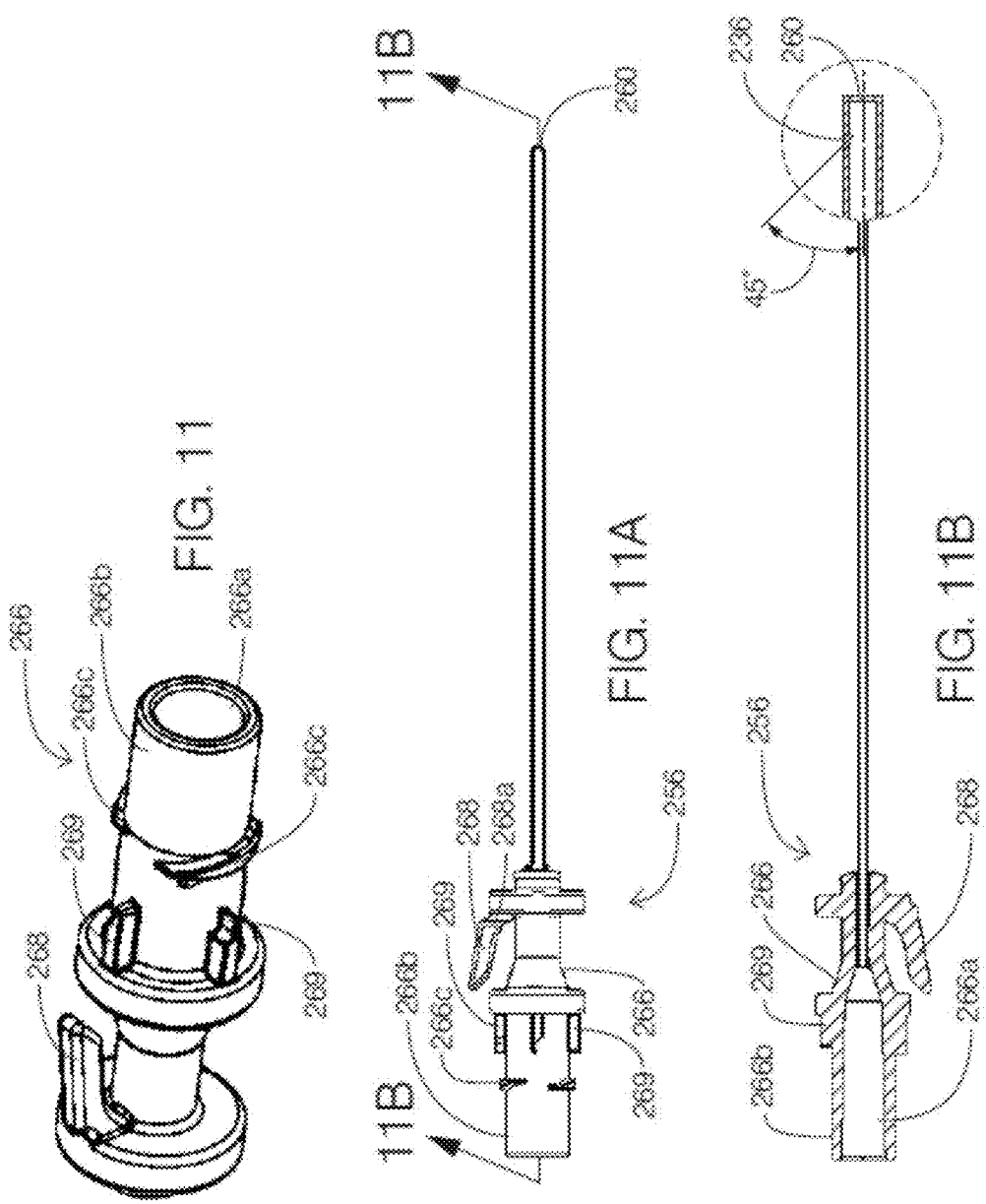

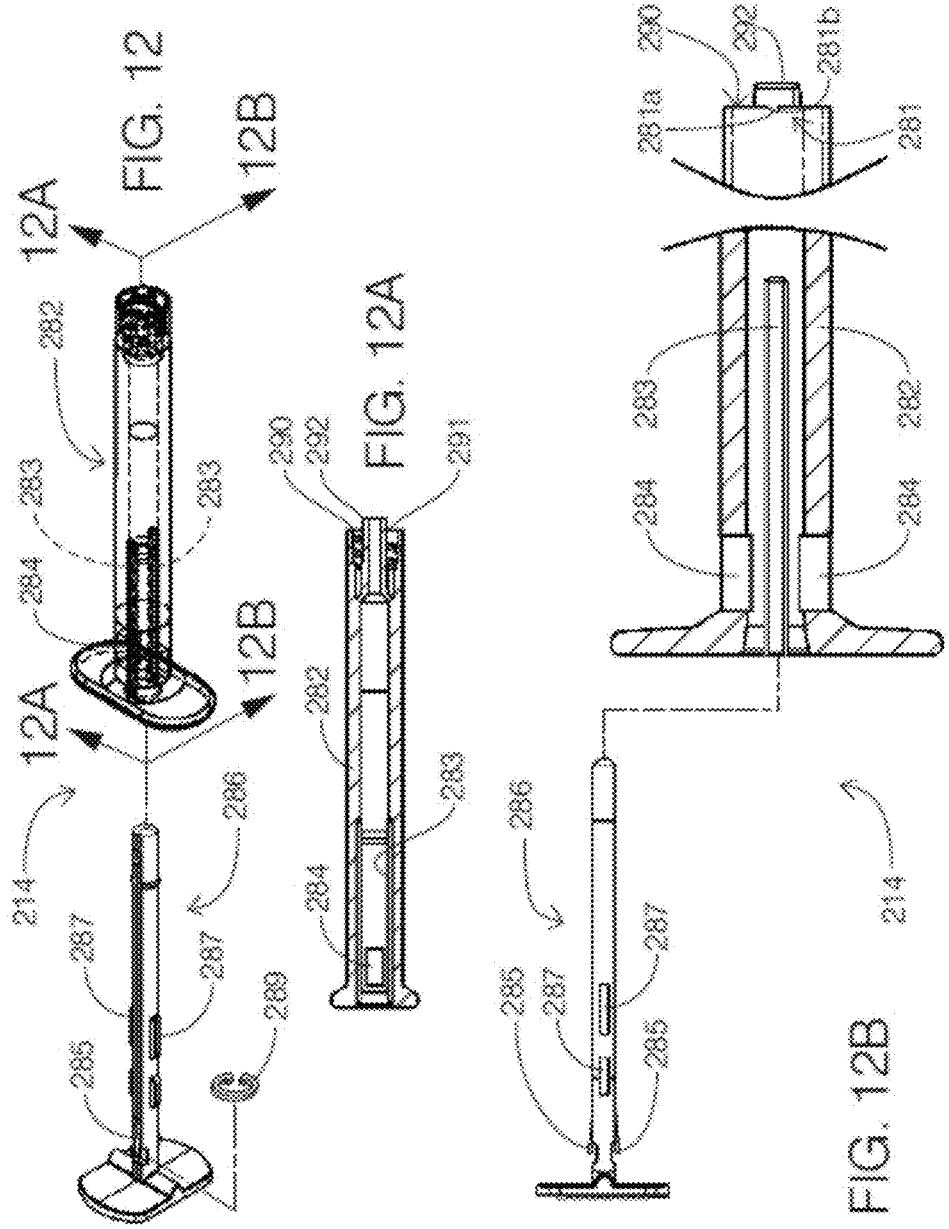

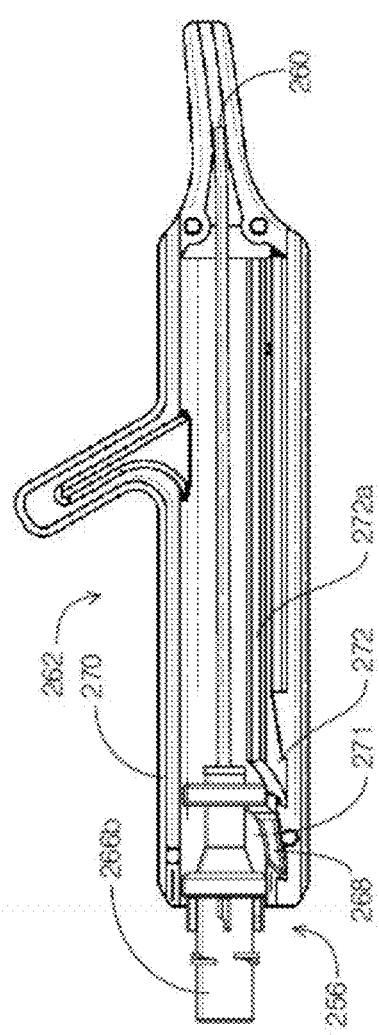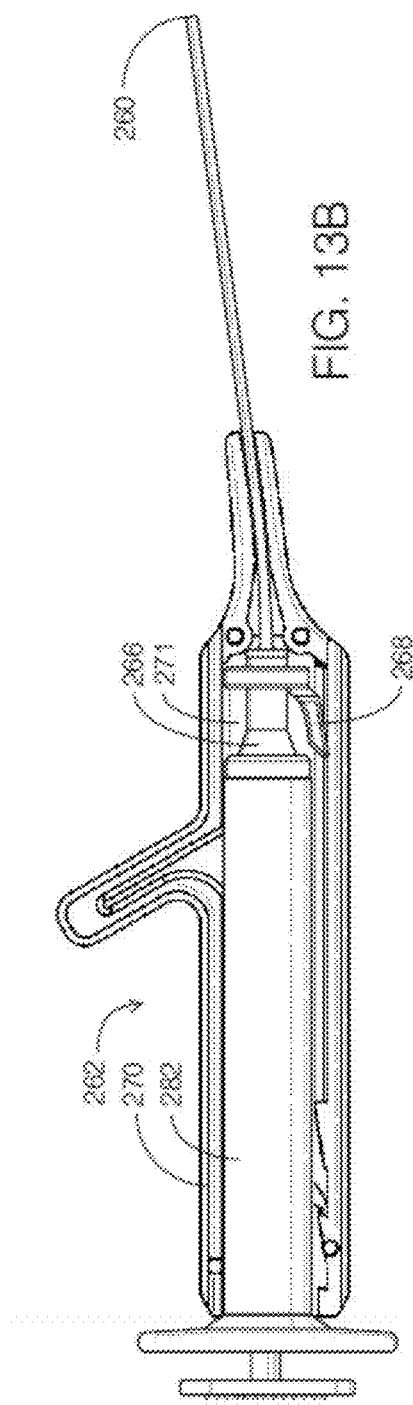

METHOD FOR TRANSNASAL DELIVERY OF BLOOD-BRAIN BARRIER PERMEATION AGENT AND THERAPEUTIC AGENT

CROSS-REFERENCE TO RELATED APPLICATIONS

This application claims priority to U.S. Provisional Patent Application No. 62/243,477, filed on Oct. 19, 2015, which is incorporated herein in its entirety by express reference thereto.

TECHNICAL FIELD

Embodiments disclosed herein generally relate to a method of treatment for diseases and disorders of the brain in a mammal. More particularly, embodiments described herein are directed to transnasal delivery of a first pharmaceutical agent enhancing blood-barrier permeability and delivery of a second pharmaceutical agent treating one or more diseases or disorders of the brain and/or other portion of the central nervous system.

BACKGROUND

For many years, reversible acetylcholinesterases (AChE) have been a highly viable target for the symptomatic improvement in Alzheimer's disease (AD) because cholinergic deficit is a consistent and early finding in AD. Other brain associated and neurological disorders including myasthenia gravis have shown therapeutic response to AChE inhibition. In particular dementia symptoms (memory and language deficits) associated with AD and Parkinson's Disease have been responsive to AChE inhibitor treatments. Although all symptoms of these and other brain diseases and disorders are not fully understood, cholinergic deficit is an early and consistent finding in AD, and it is correlated with Parkinson's Disease dementia, Lewy body dementia, and vascular dementia. During healthy brain function, acetylcholine is released into the synaptic cleft, where it can bind to a post-synaptic receptor and then be split into acetate and choline. Choline can then be pumped back into the pre-synaptic terminal by its transporter to be reused for new synthesis. Keeping a steady cycle of acetylcholine in the hippocampus helps maintain memories.

There are two types of cholinesterase, AChE and butyrylcholinesterase (BuChE). AChE is primarily in the blood and neural synapses, but BuChE is primarily in the liver. The biggest difference between these two cholinesterases is the substrates: AChE breaks down acetylcholine (ACh) more quickly, while BuChE breaks down butyrylcholine (BuCh) more quickly. Brain-targeted BuChE inhibitors have been developed based on binding domain structures to help researchers understand and apply the role of this enzyme in the central nervous system. Because oral medications including cholinesterase-inhibiting pharmaceutical agents can include gastrointestinal side effects (nausea, vomiting, diarrhea), transdermal applications have been developed including those described in U.S. Pat. Nos. 5,391,375; 5,972,376; 6,254,883; 6,316,023; and 6,335,031; each of which is incorporated herein by reference. Intranasal administration of cholinesterase inhibitors has been experimented with and reported, but those reports are directed toward general mucosal absorption and/or targeting olfactory nerves, without delivery modalities that would target specific regions (e.g., the pterygopalatine ganglion in the pterygopalatine fossa).

Some medicaments including pharmaceutical agents that inhibit cholinesterases (e.g., galantamine, donepezil, huperzine, rivastigmine, tacrine, physostigmine) may cross the blood-brain barrier, unlike many other compounds. This provides known benefits for targeting central nervous system (CNS) tissues. However, the modes of delivery and efficacy for such therapies have not fully yet been realized.

In view of certain side effects associated with oral ingestion of AChE inhibitors and the need to target the brain for alleviating specific symptoms, it may be desirable to provide a mode of delivery that is effective for treating and at least alleviating symptoms and/or causes of one or more of seizure, stroke, Parkinson's Disease, Alzheimer's Disease, multiple sclerosis, vascular dementia, idiopathic senile dementia, multiple sclerosis, benign and cancerous brain tumors, headache, Amyotrophic Lateral Sclerosis, Adrenoleukodystrophy (ALD) (including Childhood Cerebral Adrenoleukodystrophy (CCALD)), schizophrenia, and bipolar disorder, and more particularly, it may be desirable to provide known treatment regimen of pharmaceutical agent as a secondary agent after a first agent is used to temporarily increase the permeability of the blood brain barrier of a mammal receiving treatment.

SUMMARY

In one aspect, embodiments disclosed herein may include methods for treating tissue of a human or other mammalian subject, including steps of transnasally administering to the subject a first pharmaceutical agent in an amount effective to increase blood-brain barrier permeability above an initial default permeability state to a second, more-permeable state for a dose-dependent limited time; and thereafter administering to the subject a second pharmaceutical agent in an amount that is therapeutically effective to measurably reduce one or more symptoms of a brain tissue disorder; wherein, of the transnasal administration steps includes targeted spraying from within a posterior portion of the nasal cavity directed laterally and superiorly toward the sphenopalatine ganglion, preferably such that at least most of the first agent is delivered onto nasal mucosa immediately overlying the sphenopalatine ganglion. In certain embodiments, the first pharmaceutical agent may be any cholinesterase inhibitor, and in further embodiments, the first pharmaceutical agent may comprise galantamine, donepezil, huperzine, rivastigmine, tacrine, physostigmine, insulin, or a combination thereof.

In another aspect, embodiments disclosed herein may include a method for treating a disorder in a human subject, including steps of transnasally administering to the subject a first pharmaceutical agent in an amount effective to increase blood-brain barrier permeability above an initial default permeability state to a second, more-permeable state for a dose-dependent limited time; then, thereafter administering a therapeutically effective amount—for treating one or more brain tissue disorders known to be associated with brain function (including at least seizure, stroke, Parkinson's Disease, Alzheimer's Disease, multiple sclerosis, vascular dementia, headache, Amyotrophic Lateral Sclerosis, Adrenoleukodystrophy (ALD) (including Childhood Cerebral Adrenoleukodystrophy (CCALD)), major depression, multiple personality disorder, bipolar disorder, and/or any other physiological or psychiatric disorder known to be responsive to treatment with a CNS-acting pharmaceutical agent)—of a second pharmaceutical agent by administering the second pharmaceutical agent. In some embodiments, the second pharmaceutical agent may be delivered in a standard manner for a CNS-acting agent (although a lower than standard dosage may be effective in view of BBB permeabilization, regardless of the dosage modality used—e.g., oral, intravenous, intramuscular, buccal, rectal, intranasal, or other, including that the second pharmaceutical agent may likewise be transnasally delivered in a targeted manner to/toward the sphenopalatine ganglion of a subject).

In certain embodiments a method for treating a human subject, may include steps of providing a transnasal means for delivering a first pharmaceutical agent and a second pharmaceutical agent in a targeted manner to the sphenopalatine ganglion of a subject; transnasally administering a first pharmaceutical agent in an amount effective to increase blood-brain barrier permeability and immediately thereafter transnasally administering therapeutically effective amount of a second pharmaceutical agent for reducing symptoms of one or more disorders known to be associated with brain tissue function comprising seizure, stroke, Parkinson's Disease, Alzheimer's Disease, multiple sclerosis, vascular dementia, headache, Amyotrophic Lateral Sclerosis, Adrenoleukodystrophy (ALD) (including Childhood Cerebral Adrenoleukodystrophy (CCALD)), schizophrenia, major depression, multiple personality disorder, bipolar disorder, and/or any other physiological or psychiatric disorder known to be responsive to treatment with a CNS-acting pharmaceutical agent.

Another aspect is a method for delivering a pharmaceutical agent to the brain comprising contacting a subject's sphenopalatine ganglion (SPG) with a cholinesterase inhibitor and administering a therapeutically effective dose of a pharmaceutical agent to the subject. In one embodiment, the cholinesterase inhibitor comprises one or more of physostigmine, neostigmine, pyridostigmine, ambenonium, demecarium, rivastigmine, galantamine, caffeine, donepezil, tacrine, edrophonium, huperzine A, ladostigil, ungeremine, lactucopicrin, or a combination thereof. In another embodiment, the pharmaceutical agent comprises a CNS-acting pharmaceutical agent.

Another aspect is a method for permeabilizing a subject's blood brain barrier comprising contacting the subject's sphenopalatine ganglion (SPG) with a cholinesterase inhibitor. In one embodiment, the cholinesterase inhibitor comprises one or more of physostigmine, neostigmine, pyridostigmine, ambenonium, demecarium, rivastigmine, galantamine, caffeine, donepezil, tacrine, edrophonium, huperzine A, ladostigil, ungeremine, lactucopicrin, or a combination thereof. In another embodiment, the contacting is performed by transnasal administration. In another embodiment, the transnasal administration comprises using a delivery device that comprises: an injector including a first end configured to remain outside a nasal passage of the subject and a second end configured for entry into the nasal passage of the subject, where the second end is configured for fluid communication with a syringe; and an introducer configured for engagement partially into a nostril of the subject; where a distal portion of the injector includes a lateral-side aperture through which the first or the second pharmaceutical agent is to be sprayed. In another embodiment, a therapeutic pharmaceutical agent is co-administered to the subject. In another embodiment, the therapeutic pharmaceutical agent comprises a CNS-acting pharmaceutical agent. In another embodiment, the co-administration is oral, sublingual, topical, transdermal, ophthalmic, otic, nasal, rectal, vaginal, intramuscular, subcutaneous, intradermal, intravenous, intrathecal, epidural, or a combination thereof.

Another aspect is a method for treating a subject suffering from a CNS disease or disorder, the method comprising transnasally administering cholinesterase inhibitor to the subject's sphenopalatine ganglion (SPG) and co-administering a CNS-acting pharmaceutical agent. In another embodiment, the co-administration is oral, sublingual, topical, transdermal, ophthalmic, otic, nasal, rectal, vaginal, intramuscular, subcutaneous, intradermal, intravenous, intrathecal, epidural, or a combination thereof.

BRIEF DESCRIPTION OF THE DRAWINGS

FIG. 1 shows a cross-sectional side view of a device for delivering a medicament to a subject in need thereof prior to insertion of the device into a subject's nostril in accordance with principles described herein, and showing the location of the sphenopalatine ganglion of the subject.

FIG. 2 shows a cross-sectional top plane view of the device of FIG. 1 taken along the line 2-2.

FIG. 6 shows a side elevation of a second device for delivering a medicament to a subject in need thereof prior to insertion of the hub into the housing and with the injector in its storage position;

FIG. 7 shows a partial cross-sectional side view of the device of FIG. 6 with the injector in its storage position.

FIG. 9 shows an exploded perspective view of the device of FIG. 6.

FIGS. 10 and 10A show external embodiments of an introducer.

FIGS. 10B and 10D show additional external views. FIG. 10B shows a longitudinal section view taken along line 10B-10B of FIG. 10D. FIG. 10D shows a 90-degree rotated view of FIG. 10B along line 10B-10B and a bottom-up view of FIG. 10A.

FIG. 10C is a transverse section view taken along line 10C-10C of FIG. 10B.

FIGS. 10E, 10F, and 10G show embodiments of stop-bar-receiving channel configurations.

FIG. 11 shows an injector hub embodiment.

FIG. 11A shows an injector embodiment (inverted relative to the orientation in which it may enter the introducer of FIGS. 10-10A.

FIG. 11B shows a longitudinal section view of an injector, including a detail view of the distal end showing the side aperture thereof.

FIG. 12 shows a syringe assembly including a plunger oriented/rotated 90° relative to the barrel that receives it.

FIG. 12A shows a longitudinal section view of the syringe barrel.

FIG. 12B shows the assembly with a different view angle of the plunger and a relatively magnified view of the barrel that receives the plunger.

FIG. 13A shows an injector engaged into an introducer in a storage position.

FIG. 13B shows a syringe attached to an injector that is in an engaged position within and relative to an introducer such that the barrel of the syringe is substantially received within the introducer and the injector will be aligned for SPG-targeted delivery (when used as directed transnasally).

DETAILED DESCRIPTION

Figure 3:
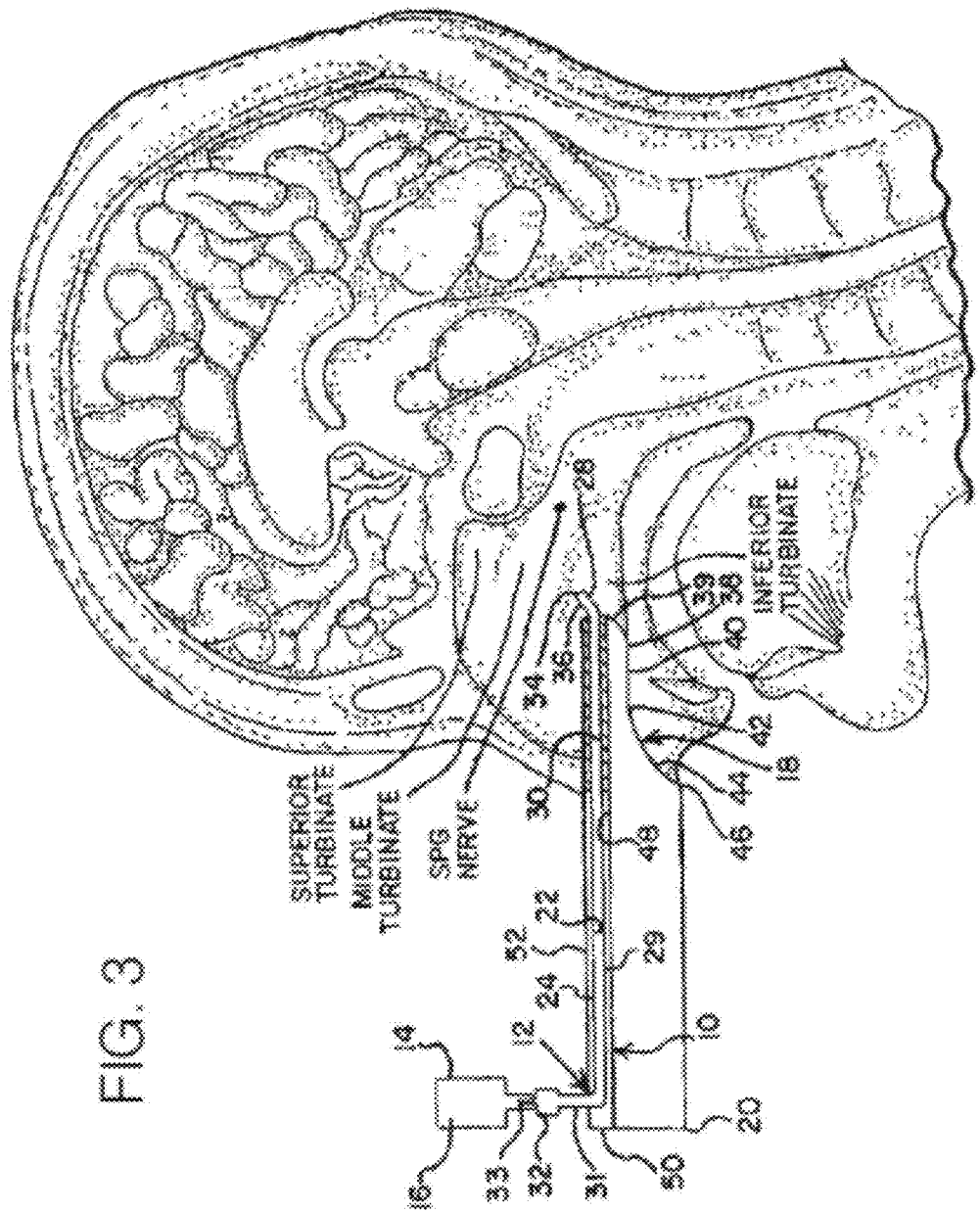
FIG. 3 shows a cross-sectional side view of the device of FIG. 1 after the introducer has been engaged with a subject's nostril in accordance with principles described herein.

Various embodiments are described below with reference to the drawings in which like elements generally are referred to by like numerals, and those elements should be considered as exchangeable and/or able to be combined between and among all the embodiments disclosed herein. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). The terms "proximal" and "distal" are used herein in a common usage sense where they refer respectively to a handle/doctor-end of a device or related object and a tool/subject-end of a device or related object. The term "superior" refers directionally to the top of a subject's head, while "inferior" refers to the opposite direction, toward the subject's feet. The term "anteriorly" refers to the direction towards the subject's face/caudal body surface, while "posteriorly" refers to the opposite direction towards the subject's back/dorsal body surface. The term "laterally" refers to left-right relative to the subject's body. The term "about" when used with reference to any volume, dimension, proportion, or other quantitative value is intended to communicate a definite and identifiable value within the standard parameters that would be understood by one of skill in the art (equivalent to a medical device engineer with experience in the field of medicament/pharmaceutical agent delivery devices and/or a pharmacist experienced in methods of solution/suspension and delivery of medicaments), and should be interpreted to include at least any legal equivalents, minor but functionally-insignificant variants, and including at least mathematically significant figures.

The term "therapeutically effective amount" as used herein refers to that amount of a compound being administered which will relieve to some extent one or more of the symptoms of the disorder being treated. Relief of symptoms may be quantified using one or more of subject self-reporting regarding severity of symptoms, tracking of disorder incidence frequency and/or severity (e.g., epileptic seizure, alcohol use, cocaine use, binge eating occurrence, etc.), and/or diagnostic testing means known in the medical art including at least those for evaluating subject behavior, blood chemistry, cell/tissue biopsy samples, and other standard medical diagnostic evaluation means. The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a mammal. The term/phrase "CNS-acting pharmaceutical agent" and similar phrases refers to and is intended to include any/all pharmaceutical agents that are known or developed in the art of treating subjects with CNS-involved disorders (including mental, physical, and/or psychiatric diagnoses) where the agent is known, generally believed, or predicted to act directly and efficaciously upon CNS tissue, including CNS-specific agents that target one or more cells or tissues of the central nervous system, and other agents that are not CNS-specific but that are known, generally believed, or predicted to have an efficacious effect for the subject by interaction with the central nervous system. In this context, the terms "known, generally believed, or predicted" are used and defined in a manner that should clearly indicate to those in the medical, pharmaceutical, and/or pharmacological arts that there is a documented clinical belief or prediction, and/or that the known or predicted structure of such agent(s) is expected or known to interact with one or more receptors of CNS tissue cellular material, or otherwise interact with CNS tissue, most preferably in an efficacious manner.

As used herein, the phrase "towards the sphenopalatine ganglion" (SPG) and similar such phrases used in reference to the delivery of a medicament are intended to include the SPG itself as well as the pterygopalatine fossa which houses the SPG and the sphenopalatine foramen, such that delivery of a medicament described herein shall be understood to refer to the location and/or directionality of delivery that results directly in applying the medicament to the SPG (e.g., via overlying tissue of the nasal mucosa, which overlying tissue should be understood as being included when the present disclosure references delivery to/toward the SPG). It is believed that the proximity of the SPG and surrounding tissue to the brain, including shared circulatory vessels relates to the enhanced efficacy at low dosages of the medicament treatment described herein, where the term "low" is used relative to standard peroral dosages at the levels prescribed for disorders being treated with the present method embodiments. In one embodiment "low" refers to a dose of about 0.5 to about 0.01 of a standard peroral dose.

It has been discovered that a method of novel transnasal delivery of an AChE increases blood-brain barrier permeability for a dose-dependent limited time. This provides for unexpectedly enhanced efficacy of a second pharmaceutical agent (that is known to be effective at treating one or more ailments by interaction with/upon CNS tissue) by providing direct access across the blood-brain barrier (BBB) at a level lower other known dosing sources or regimens where the concentration must be higher to effect crossing the BBB, and/or another mode of introduction is used. For example, certain other regimens have used nanoparticles, emulsions, and/or liposomal complexes to traverse the BBB, including with introduction via olfactory and/or trigeminal nerves, each of which is different than embodiments of the present method that target the SPG with delivery of a simple aqueous solution. Complexes, constructs, solutions, and the like that include nanoparticles, emulsions, BBB, liposomes, and/or other materials used in other BBB-traversing treatment modalities may be useful within the scope of the present method including that one or more of them may be targeted to the SPG using a device of the type embodied and described herein.

The healthy BBB generally provides an optimally controlled homeostasis of the brain's internal environment. Its anatomical structure including of the gliovascular complex with tight junctions between the endothelial cells enables a very selective transport of substances from the blood to the brain by any of the following routes: (1) paracellular waterway through the tight junctions for hydrophilic substances of less than 180 Da molecular weight; (2) transcellular diffusion of lipophilic substances; (3) transcellular route using transport proteins, e.g., glucose, some amino acids; (4) endocytosis mediated by specific receptors, e.g., for insulin, transferrin; (5) adsorptive endocytosis and transcytosis for cationized plasma proteins, i.e., transport vesicles.

Delivery of a cholinesterase inhibitor at a low dosage is be effective for permeabilizing the BBB. By way of illustration, a rat model was used to test certain embodiments of the present method. In this experiment, normal saline solution (0.90% w/v NaCl in water) was used as a control, and three different concentrations of a cholinesterase inhibitor (rivastigmine) were administered transnasally to permeabilize the BBB of the rat test subjects. Then, to test permeabilization, a solution of Evans Blue dye (molecular weight=960.81 kDa; available from Sigma-Aldrich) was administered intravenously, with the rats' brain tissue being evaluated to determine the permeabilization by cholinesterase inhibitor dosage concentration, and over time. The increased permeabilization lasted about one hour. The data table below shows the test results with standard deviation bars (p=0.0158). As shown, treatment with saline followed by intravenous administration of Evans Blue provides a low-level baseline for comparison with the cholinesterase inhibitor dosages, where the treatment with 1 mg/kg provided the greatest permeabilization as measured by presence of Evans Blue dye in the rat brain tissue after parallel consistent treatments under the different dosages shown. The "mg/kg" dosage was metered to the weight of each rat being tested, and the μg/mg dry weight measures the Evans Blue in harvested CNS tissue. See FIG. 14B.

Based on studies in rats using Evans Blue, the second agent can have a molecular weight of at least 1000 kDa. Evans blue is typically bound to serum albumin and when the BBB is permeabilized as described herein, albumin-bound Evans Blue passes through the BBB.

Based upon known differences in sensitivity and model system efficacy, it is expected that effective dosage of a human subject for BBB permeabilization would occur at this dosage down to about one tenth to about one hundredth of the dosage described above. As such, the present method of treatment is expected to be effective for treating and at least alleviating symptoms (and/or causes) of brain-related disorders including one or more of at least Lewy body dementia, vascular dementia, seizure, stroke, Parkinson's Disease, Alzheimer's Disease, multiple sclerosis, headache, Amyotrophic Lateral Sclerosis, Adrenoleukodystrophy (ALD) (including Childhood Cerebral Adrenoleukodystrophy (CCALD)), vascular dementia, idiopathic senile dementia, multiple sclerosis, benign and cancerous brain tumors, schizophrenia, major depression, multiple personality disorder, bipolar disorder, and/or any other physiological or psychiatric disorder known to be responsive to treatment with a CNS-acting pharmaceutical agent. More particularly, it may be desirable to provide a treatment regimen of known CNS-acting pharmaceutical agent as a secondary agent after a first agent is used to temporarily increase the permeability of the blood brain barrier of a mammal receiving treatment. That is, one or more pharmaceutical agent(s) may be delivered after BBB permeabilization via the SPG using the presently-described method, where the pharmaceutical agent(s) is/are known to have CNS-tissue (including CNS-tissue-specific) efficacy, and the presently disclosed method for BBB permeabilization will provide for effective delivery, often at a lower dosage and/or with lower risks than known pharmaceutical treatment methods (even superior those including the exact same secondary pharmaceutical agents as compared to when such are delivered in another method).

Otherwise stated, in view of the animal model experimental data reported here with the other disclosure provided herein, and taking into account the current sophisticated state of the art of medical pharmacological treatments for brain-related disorders, the present disclosure sets forth a novel and elegant method for increasing or even optimizing the efficiency of CNS-active pharmaceutical agents by providing a simple, effective, and safe method for temporarily increasing the permeability of the BBB. In view of the present disclosure, those of skill in the art will be able to perform a method of transnasal delivery targeted to the SPG of a first pharmaceutical agent that will permeabilize (that is, will temporarily increase the permeability of) the blood-brain barrier. In addition to this step, a practitioner may administer a CNS-active second pharmaceutical agent in a manner that provides for effective delivery of that second agent to the brain and/or other CNS tissue. This manner may include intramuscular, intravenous, oral, sublingual, buccal, rectal, intra-nasal, trans-nasal targeting the SPG, perfusion into a peritoneal or other body cavity, or any other manner of introducing a second agent, where that agent will enter the bloodstream and be present at a concentration in the bloodstream effective to cross the permeabilized BBB and effective to treat a subject condition. The effective bloodstream concentration of the second agent will, in view of the permeabilized BBB, be lower than generally acknowledged as effective via the same mode of administration without the permeabilized BBB of the present method. (For example, an effective dosage of a second pharmaceutical typically administered intravenously at a concentration of "X mg/mL"

is expected to be effective at a dosage of "less than X mg/mL," where the reduction may be a single digit percentage, but generally is expected to be at least a double-digit percentage to one or more orders of magnitude).

The therapeutically effective amount of the second agent will vary depending upon the identity thereof, as will the frequency of dosing administration. An effective regimen may include administering a predetermined dosage of the second pharmaceutical agent once or several times per day, once or several times per week (preferably delivered at 0.5 times the dosage per nostril, if delivered transnasally to the SPG in the manner of the initial BBB-permeabilization dosage). Effective dosage may include administering up to a known maximum safe dosage, with an effective dosage range expected to include only a small fraction of that maximum due to the enhanced BBB permeability that will require a lower serum concentration of the second agent in the subject's blood, and expressly including each and every dosage level between an effective minimum and a dosage maximum, as well as any and all subranges thereof, where effective dosage may vary depending upon the subject and the specific indication being treated.

The effective dosage of the first pharmaceutical agent for BBB permeabilization may also vary, but may be a human subject about on the order of about 0.1 mg/kg (first pharmaceutical agent/subject mass) when rivastigmine is used.

As known for treatment regimens using various CNS-active pharmaceutical agents, dosage may remain level through multiple administrations over a period of days, weeks, months, etc., or the dosage may be increased or decreased in keeping with the therapeutic efficacy and incidence—if any—of side effects, under the guidance and supervision of a physician. In certain preferred embodiments, the effective amount is in an aqueous solution or suspension of about 0.1 mL to about 1 mL of total volume, although the volume may be up to about 5 mL. In one method, about one-half of the solution is delivered to the SPG via a right nostril of a subject, and the remaining solution is delivered to the SPG via the left nostril of the subject. In other methods, a first portion of the complete dosage may be delivered to one nostril, and a second portion (preferably completing a complete dosage) may be delivered to the other nostril.

Various cholinesterase inhibitors may be useful (alone or in any combination) for enhancing BBB permeability via delivery thereof to the SPG. The solubility of galantamine (as an HBr salt) in water is known to be about 10 mg/mL, with different solubility in lactate form. The solubility of donepezil in water is known to be about 0.00293 mg/L. The solubility of huperzine in water is known to be about 0.188 mg/mL. The solubility of rivastigmine in water is known to be about 2.04 mg/mL. The solubility of tacrine in water is known to be about 0.217 mg/mL. The solubility of physostigmine in water is known to be about 7.76 mg/mL. Methods of preparation may include obtaining one of these or another cholinesterase inhibitor in tablet form (e.g., in the form of an oral tablet as commercially available), grinding it into powder, and dissolving or suspending it into water or a water-based solution that may include saline or other materials including soluble excipients from a tablet or capsule. These methods will provide for easily-obtainable dosage forms for the present method using resources available through standard commercial avenues. If desired, standard extraction methods may be used to remove one or more excipients from, for example, ground-up oral-dosage form(s) of the cholinesterase inhibitor before administration to a subject. Alternatively, the active pharmaceutical ingredient may be supplied in a pure dry form suitable for placing into liquid deliverable form as described herein (e.g., upon compounding by a pharmacist or physician), may be supplied in a dosage-ready liquid form, or may be supplied in a concentrated/water-dilutable liquid form.

While neither being bound by any particular theory, nor intending to affect in any measure the scope of the appended claims or their equivalents, the following background information is provided regarding present-day understanding of the anatomy of the SPG in order to further elucidate the description of the devices and methods provided herein below. The SPG (also known as the pterygopalatine ganglion) is the largest group of neurons outside the cranial cavity and lies in the pterygopalatine fossa, which is approximately 1-cm wide and approximately 2-cm high. The pterygopalatine fossa is bordered anteriorly by the posterior wall of the maxillary sinus, posteriorly by the medial plate of the pterygoid process, medially by the perpendicular plate of the palatine bone, and superiorly by the sphenoid sinus. Laterally, the pterygopalatine fossa communicates with the infratemporal fossa.

The SPG within the fossa is located posterior to the middle turbinate of the nose and lies a few millimeters (1 mm to 5 mm) deep in the lateral nasal mucosa. The SPG has a complex neural center and multiple connections. The SPG is suspended from the maxillary branch of trigeminal nerve at the pterygopalatine fossa via the pterygopalatine nerves, and lies medial to the maxillary branch when viewed in the sagittal plane. Posteriorly, the SPG is connected to the vidian nerve. The SPG itself has efferent branches and forms the superior posterior lateral nasal and pharyngeal nerves. Caudally, the ganglion (SPG) is in direct connection with the greater and lesser palatine nerves. Stated differently, the SPG is a small concentrated structure of neuronal tissue that resides within the pterygopalatine fossa (PPF) in close proximity to the sphenopalatine foramen. The SPG is innervated by the maxillary division of the trigeminal nerve and has a sensory, parasympathetic, and sympathetic component. Access to this structure can be gained via a small area of mucosa just posterior and superior to the tail of the middle turbinate on the lateral nasal wall.

The SPG has sensory, motor and autonomic components. The sensory fibers arise from the maxillary nerve, pass through the SPG, and are distributed to the nasal membranes, the soft palate and some parts of the pharynx. A few motor nerves are also believed to be carried with the sensory trunks.

The autonomic innervations of the SPG are more complex. The sympathetic component begins with preganglionic sympathetic fibers originating in the upper thoracic spinal cord, forming the white ramie communicantes, coursing through the sympathetic ganglion, where the preganglionic fibers synapse with the postganglionic ones. The postganglionic fibers then join the carotid nerves before branching off and traveling through the deep petrosal and vidian nerves. The postganglionic sympathetic nerves continue their path through the SPG on their way to the lacrimal gland and nasal and palatine mucosa.

The SPG is usually considered parasympathetic in function. The parasympathetic component of SPG has its preganglionic origin in the superior salivatory nucleus then travels through a portion of the facial nerve (VII) before forming the greater petrosal nerve to form the vidian nerve, which ends in the SPG. Within the ganglion, the preganglionic fibers synapse with their postganglionic cells and continue on to the nasal mucosa, and one branch travels with the maxillary nerve to the lacrimal gland.

Notwithstanding the description above, and regardless of the currently-held theories respecting the anatomy of the SPG, a safe and effective treatment of obesity can be achieved as a result of using the devices and methods described below. Although representative devices 10, 54, and 254 are be described in reference to FIGS. 1-4 and FIGS. 6-13B, respectively, it is to be understood that these representative devices are merely illustrative and that alternative structures can likewise be utilized for delivering a medicament in accordance with principles described herein. It is to be understood that elements and features of the various representative devices described below may be combined in different ways to produce new embodiments that likewise fall within the scope of the present teachings. The drawings and the description below have been provided solely by way of illustration, and are not intended to limit the scope of the appended claims or their equivalents.

Figure 4:
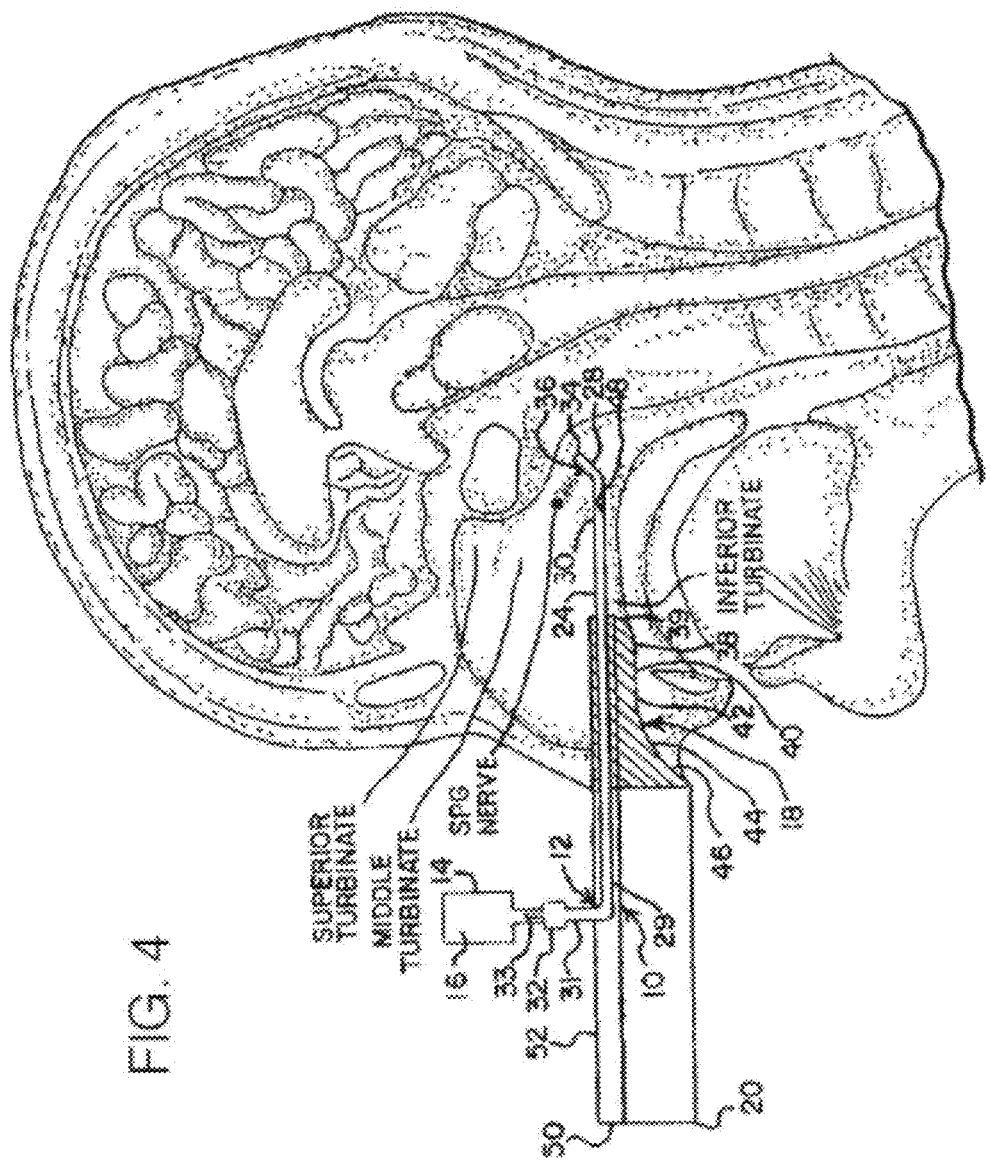
FIG. 4 shows a cross-sectional side view of the device of FIG. 1 after the introducer has been engaged with a subject's nostril and after the injector has been moved from its storage position to an engaging position that positions the second end of the injector medial, posterior, and inferior to the sphenopalatine ganglion.
Figure 5:
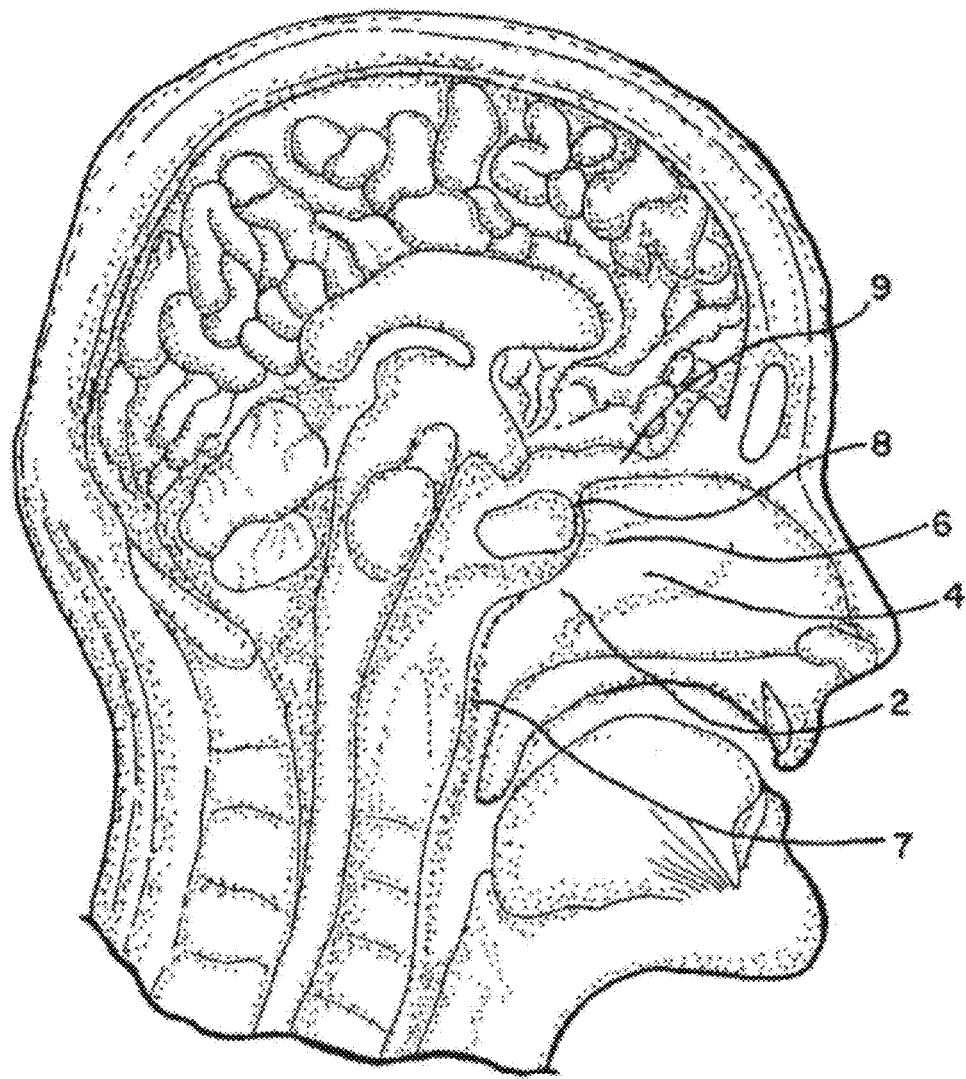
FIG. 5 shows a median cross-sectional view of a human head with the SPG shown in its correct anatomical position posterior to the middle turbinate.

FIGS. 1-4 show a representative device 10 for delivering a medicament to a subject in need thereof. The device 10 includes an injector 12 comprising a first end 29 configured to remain outside a nasal passage of the subject and a second end 30 configured for entry into the nasal passage of the subject. Device 10 further includes an introducer 18 configured for engagement with a nostril of the subject and comprising a passageway 48 configured for slidably receiving the injector 12. The injector 12 is moveable between a storage position (best shown by FIG. 1) preceding engagement of introducer 18 with a subject's nostril, and an engaging position (best shown by FIG. 4) pursuant to engagement of introducer 18 with the subject's nostril. However, upon the initial engagement of introducer 18 with a subject's nostril, the injector 12 is desirably maintained—at least for a time—in a storage position (best shown by FIG. 3) until it is deliberately moved to an engaging position (best shown by FIG. 4) under the direction of a user. In some embodiments, the engaging position of injector 12 is situated medial and/or inferior to the SPG. In other embodiments, the engaging position of injector 12 is situated medial, inferior, and posterior to the SPG, as best shown by FIG. 4.

As used herein, the phrases "storage position" and "engaging position" are each intended to encompass multiple positions within a selected range. For example, in some embodiments, the degree to which injector 12 is extended into the nostril of a first subject (e.g., a child) will vary from the degree to which injector 12 is extended into the nostril of a second subject (e.g., an adult male). Notwithstanding, the phrase "engaging position" is intended to encompass many variations in the precise position of injector 12 within the nostril, any of which are properly regarded as being medial and/or posterior and/or inferior to the SPG. In some embodiments, injector 12 is not slidable within introducer 18 but rather is fixed in a predetermined position so as to be medial and/or inferior to the SPG upon engagement of introducer 18 with a subject's nostril. In other embodiments, injector 12 is not slidable within introducer 18 but rather is fixed in a predetermined position so as to be medial, posterior, and inferior to the SPG upon engagement of introducer 18 with a subject's nostril.

The injector 12 comprises a tubular section 24 (a so-called cobra tube in recognition of the tube's extensibility) that includes a channel 22 extending from first end 29 to second end 30 and configured for receiving a medicament. In some embodiments, tubular section 24 has an outer diameter of about 5 mm and channel 22 has an inner diameter of about 2 mm. Throughout this description, measurements and distances such as the diameters just given are to be strictly regarded as being merely representative and in no way limiting and/or fixed. Considerable variation in all measurements and distances provided in this description is possible, as will be readily appreciated by one of ordinary skill in the art.

In some embodiments, the second end 30 of injector 12 contains a nozzle 28 having a tip 34 that contains one or a plurality of apertures 36 configured for spraying a medicament superiorly and/or laterally and/or anteriorly towards the SPG. In some embodiments, nozzle 28 is configured for spraying a medicament laterally and/or superiorly towards the SPG, and in other embodiments, nozzle 28 is configured for spraying a medicament laterally, superiorly, and anteriorly towards the SPG. Spraying includes directing in a stream, mist, or anything in between, subject to the size/shape of the delivery aperture, viscosity of the liquid being delivered, and the pressure administered thereto. Most preferably, and to maintain efficacy and efficiency with regard to targeting the SPG and delivering a smallest effective dose, the spray is directed laterally and/or superiorly, and anteriorly, but not posteriorly.

In some embodiments, nozzle 28 extends at an upward angle of inclination from second end 30 of injector 12. In some embodiments, nozzle 28 extends in a lateral, anterior, and superior direction at an angle of inclination ranging from about 45 degrees to about 60 degrees to accommodate varying subject anatomies in which the SPG resides in a lateral cave posterior to the middle turbinate. In some embodiments, nozzle 28 has a length ranging from about 2 mm to about 5 mm. In some embodiments, injector 12 is designed to exhibit handedness, such that in some embodiments, injector 12 is configured for engagement with a left-side nostril of a subject, whereas in other embodiments, injector 12 is configured for engagement with a right-side nostril of the subject (with the contour of a left-handed injector being generally complementary to the contour of a right-handed injector).

The introducer 18 can be aimed into a nostril to provide a horizontal pathway substantially parallel to the bottom of the nasal cavity or floor of the nose—such that introducer 18 is supported on the bottom of the nasal cavity—to a position medial to the inferior turbinate. This self-seating feature of introducer 18 facilitates quick and accurate usage by a subject without necessitating supervision from a medical professional. In some embodiments, introducer 18 provides an extended pathway of between about 1.5 cm and about 2 cm into the nostril. Once introducer 18 is placed firmly against the nose, the tip of the nose will tend to point superiorly. The tubular section 24 of injector 12 can then be pushed partially or completely into the back of the nostril. In order to accommodate the slightly curved nature of the interior anatomy of the nose, the passageway 48 in which tubular section 24 lies can be curved slightly to the ipsilateral nostril by about 5 to about 20 degrees. Once tubular section 24 is in position (that is preferably having been advanced below and along the middle turbinate just past the pterygopalatine fossa into the intranasal space), a medicament can then be delivered to the SPG from nozzle 28 to exert the desired SPG blocking effect, or to provide a different therapeutic effect or enhancement thereof. For example, in certain of the present embodiments, delivery of a cholinesterase inhibitor, insulin, or other material via this method may provide a temporally limited effect of increasing blood-brain barrier permeability so that a pharmaceutical agent known to have CNS tissue efficacy can be delivered in the same manner. In some embodiments, device 10 is provided with an optional safety abutment stop to limit the extent of travel into the nostril available to injector 12.

As best shown by FIGS. 1, 3, and 4, introducer 18 contains a first portion 44 and a second portion 38. In some embodiments, a cross-sectional area of first portion 44 is larger than a cross-sectional area of second portion 38. In some embodiments, first portion 44 is generally concave and has a contour 46 configured to be complementary in shape to an interior of the nostril so as to substantially conform therewith. In some embodiments, narrow second portion 38 has a rounded convex portion 39 and an underside 40 having a generally flat surface 42. The passageway 48 of introducer 18 slidably receives tubular section 24 of injector 12 and, in some embodiments, has a diameter of between about 6 mm and about 7 mm. In some embodiments, second portion 38 of introducer 18 contains a nostril-engaging tip that extends from about 1 cm to about 3 cm. In some embodiments, first portion 44 of introducer 18 extends from about 2 cm to about 3 cm. In some embodiments, introducer 18 is designed to exhibit handedness, such that in some embodiments, introducer 18 is configured for engagement with a left-side nostril of a subject, whereas in other embodiments, introducer 18 is configured for engagement with a right-side nostril of the subject (with the contour of a left-handed introducer being generally complementary to the contour of a right-handed introducer).

In some embodiments, device 10 further includes a container 14 in communication with first end 29 and channel 22 of injector 12, which is configured for holding a medicament 16 (e.g., a solution, suspension of a cholinesterase-inhibiting pharmaceutical agent, insulin, or another selected pharmaceutical agent, including any pharmaceutical salts and/or other effective variants thereof for any such agent such as, for example, lactates, citrates, and/or other compounds or complexes, but specifically excluding liposomes and chitosan carriers as used in the prior art). In some embodiments, as shown in FIGS. 1, 3, and 4, container 14 is supported on a stem 26 having a lower section 31 which, in some embodiments, has an outer diameter substantially the same as that of tubular section 24. Lower section 31 can extend outwardly and/or upwardly and/or at an angle of inclination from first end 29 of injector 12 and, in some embodiments, connects with an upper section 32 having an enlarged diameter configured to receive an outlet 33 of container 14. Analogous to lower section 31, upper section 32 can extend outwardly and/or upwardly and/or at an angle of inclination.

In some embodiments, container 14 is operatively connected, mounted or otherwise secured to upper stem section 32 and is fully or partially filled with a medicament 16. Since container 14 is in communication with channel 22 of injector 12, medicament 16 can be delivered along tubular section 24 and released through one or more apertures 36 of nozzle 28. Container 14 can be formed of plastic, metal or the like, and can be squeezable and/or pressurized to facilitate medicament delivery into channel 22. In some embodiments, container 14 is replaced by a port (not shown), such that a medicament can be introduced through the port into upper section 32 by a delivery device such as a syringe.

In some embodiments, device 10 further includes an optional handle 20 connected to a rear portion of introducer 18 adjacent first portion 44. The handle 20 includes an upwardly facing groove 50 that provides a track 52 configured to receive and in communication with passageway 48 of introducer 18 to slidably receive tubular section 24 of injector 12. In some embodiments, track 52 has a depth or width of between about 6 mm and about 7 mm. Handle 20 is configured for movement towards a subject's face, such that posterior movement of handle 20 moves introducer 18 into engagement with the nostril of the subject.

Injector 12, introducer 18, and handle 20 can be formed from all manner of materials including but not limited to flexible, rigid or semi-rigid polymeric materials (e.g., plastics, rubbers, etc.), metals and alloys thereof, and the like, and combinations thereof. In some embodiments, injector 12 is formed of a flexible plastic, introducer 18 is formed of an elastomeric and/or resilient plastic or rubber, and handle 20 is formed of plastic. In some embodiments, one or more of injector 12, introducer 18, and handle 20 is designed from a material so as to be disposable and/or biodegradable.

While the representative device 10 described above can be used to deliver a medicament superiorly and/or laterally and/or anteriorly towards a sphenopalatine ganglion of a subject in accordance with the principles set forth herein, alternative structures can likewise be employed to similarly accomplish such a delivery. For example, an injector device may include a configuration like that shown in FIG. 8, but without need for deployment, positionable for medicament delivery in the manner shown in FIG. 4. Such a device and method are contemplated herein and subject to the present claims.

By way of illustrative but non-limiting example, a delivery tube having a curved portion at one of its ends configured for insertion into a subject's nostril—analogous to the angled nozzle 28 provided on the second end 30 of injector 12—can be housed within a substantially cylindrical (e.g., pen- or cigar-shaped) housing. The delivery tube can be formed of a flexible or semi-rigid material (such as a plastic) such that it can be maintained in a substantially linear or non-curved arrangement while in its storage position within the housing but readily restored to its curved configuration when extended from the housing into an engaging position. In such a device, one or more internal surfaces of the external housing acts to straighten or restraing—completely or at least partially—the inherent curvature of the delivery tube until such time as the delivery tube is moved to an engaging position, whereupon the curvature of the tube is restored. In some embodiments, at least a portion of the delivery tube (e.g., the end designed to emit medicament) can be expandable if desired (e.g., when air, oxygen and/or other gases, and/or medicaments are forced through the tube under pressure).

By providing one or more optional indicial markings on the cylindrical housing described above, a user can readily identify the direction of curvature of the delivery tube stored inside, such that by turning the housing around and arc of 360 degrees, the user can select any desired direction of spray for delivering a medicament through the delivery tube. Simply by rotating the housing, the direction of spray can be incrementally changed through a continuous arc between 0 degrees and 360 degrees inclusive. In design, one end of the housing can be fitted with a luer lock configured to engage with a syringe containing the medicament. Alternatively, the end of the housing configured to remain outside the nostril can be fitted with a septum or similar such membrane through which a medicament can be introduced into the delivery tube housed therein.

Numerous other modifications to the delivery devices described herein, as well as alternative structures, are likewise contemplated for use to the extent they similarly allow for the delivery of a medicament superiorly and/or laterally and/or anteriorly towards a sphenopalatine ganglion of a subject in accordance with the present teachings. By way of example, the portion of the device configured for insertion into a subject's nostril (e.g., a portion of the injector 12 described above) can be formed from any therapeutically acceptable malleable material (e.g., plastics, metals, metal alloys, and the like) capable of receiving and retaining a desired shape when manipulated by a user. (e.g., increased or decreased curvature of the angled nozzle 28 provided on the second end 30 of injector 12). Such a feature may be desirable, for example, when a clinician wishes to customize the exact geometry of a device before using it on a subject in a clinical setting.

FIGS. 6-9 show a representative device 54 for delivering a medicament to a subject in need thereof. The device 54 includes an injector 56 comprising a first end 58 configured to remain outside a nasal passage of the subject and a second end 60 configured for entry into the nasal passage of the subject. Device 54 further includes an introducer 62 configured for engagement with a nostril of the subject and comprising a passageway 64 configured for slidably receiving the injector 56. The injector 56 is moveable between a storage position (best shown by FIGS. 6 and 7) preceding engagement of introducer 62 with a subject's nostril, and an engaging position (best shown by FIG. 8) pursuant to engagement of introducer 62 with the subject's nostril. It should be appreciated with reference to this illustration that a syringe or other medicament-containing/medicament-delivering device would be at least partially received into the passageway 64 as a means of (or result of) advancing the injector distally relative to the introducer. Such a device preferably is attached to and in patent fluid communication with the injector tube lumen.

Figure 8:
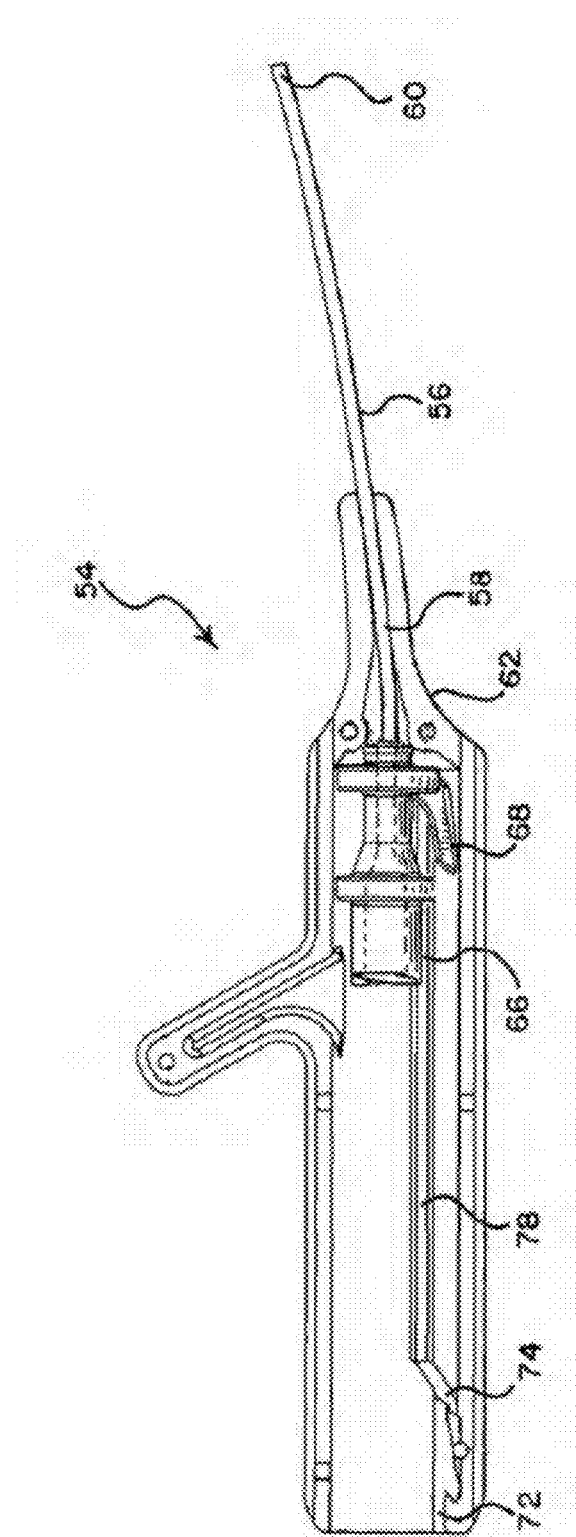
FIG. 8 shows a partial cross-sectional side view of the device of FIG. 6 with the injector in an engaging position.

As shown by FIGS. 6 and 7 (see also FIGS. 11-11B), the injector 56 (256) may be coupled to a hub 66 fitted with a luer lock mechanism configured to engage with the threads of a syringe (not shown) containing a medicament to be delivered to a subject. As best shown by FIGS. 7-9, the hub 66 is coupled to a stop bar 68 that is compressible. Prior to engagement with a syringe, hub 66 is configured to remain outside of housing 70 and to resist rotation therein since stop bar 68 is positioned within a keyed slot 72 formed by the two halves of housing 70. As hub 66 is pressed axially into housing 70 (e.g., by a syringe coupled to the luer lock mechanism on hub 66), stop bar 68 travels along keyed slot 72 until it reaches lip 74 at which point stop bar 68 engages lip 74, thereby preventing retraction of hub 66 from the interior of housing 70, and at which point hub 66 (and the syringe coupled thereto) become rotatable over a fixed range. The irreversibility of the axial travel of hub 66 within housing 70 provides a useful way for a practitioner to readily distinguish a used device from an unused one—namely, if hub 66 does not protrude from housing 70, the device has previously been used.

As may best be understood from a consideration of FIGS. 8 and 9, stop bar 68 is further configured to act in conjunction with a ledge 78 inside of housing 70 such that the range of rotation of hub 66 (and the syringe coupled thereto) is limited to predetermined angles (e.g., about 45° clockwise or 45° counterclockwise). Rotation beyond the predetermined angles (which are determined based on positioning of ledge 78) is prevented when stop bar 68 butts up against ledge 78. This feature facilitates accuracy of use by a user by limiting the positions from which medicament can be introduced from injector 56 to those having the desired trajectory towards a target site.

As best shown by FIG. 8, injector 56—which in some embodiments comprises a flexible plastic tube having shape memory—retains a slight curvature that is conferred upon it by the curved portion of the lumen 64 of the distal end of the introducer 62 during storage. By virtue of this curvature, and by providing one or a plurality of apertures along the side of second end 60, the injector 56 is designed to be used in both the left-side and right-side nostrils of a subject without regard to handedness (see, by way of illustration, aperture 236 in FIG. 11B).

In some embodiments, the diameter of the one or plurality of apertures along the side of second end 60 of injector 56 is smaller than an outer diameter of the flexible plastic tube, such that the liquid expelled through the aperture upon pressing the plunger of the syringe exits forcefully. In some embodiments, depending on the flexibility of the plastic tube, injector 56 undergoes further curvature under the pressure exerted by depression of the syringe plunger (e.g., in a direction away from that of the liquid exiting the aperture). In some embodiments, the diameter of the one or plurality of apertures is smaller than an inner diameter of the flexible plastic tube. In some embodiments, the flexible plastic tube comprises a nylon resin (e.g., such as that sold under the tradename PEBAX 72D). In some embodiments, the flexible plastic tube comprises PEBAX 72D, has an outer diameter $\Phi$ of 0.039±0.001, has a wall thickness of 0.00±0.001 (i.e., five thousandths of an inch), and has an aperture with a diameter of 0.005±0.001. In some embodiments, the aperture is oriented at a 50° angle in a direction oriented towards the hub. In some embodiments, introducer 62, housing 70, keyed slot 72, lip 74, and ledge 78 are integrally formed (in some embodiments, as two complementary molded halves press fit and/or bonded together, such as with adhesives, sonic welding or the like) and, in some embodiments, these portions comprise polycarbonate. In some embodiments, hub 66 and stop bar 68 likewise comprise polycarbonate.

A method for treating a subject in accordance with the present teachings includes delivering a medicament superiorly and/or laterally and/or anteriorly towards a sphenopalatine ganglion of a subject using a device as described herein. In some embodiments, the medicament is delivered laterally and/or superiorly towards the SPG. In other embodiments, the medicament is delivered laterally, superiorly, and anteriorly towards the SPG.

In some embodiments, a method for treating a subject includes (a) introducing an injector 12 through a nasal passage of the subject into a region substantially medial and/or posterior and/or inferior to an SPG of the subject; and (b) delivering a medicament from injector 12 superiorly and/or laterally and/or anteriorly towards the SPG. In some embodiments, injector 12 is introduced through a nasal passage of the subject into a region substantially medial and/or inferior to the SPG, whereas in other embodiments the injector 12 is introduced into a region substantially medial, inferior, and posterior to the SPG. In some embodiments, the medicament is delivered laterally and/or superiorly towards the SPG, whereas in other embodiments, the medicament is delivered laterally, superiorly, and anteriorly towards the SPG. In some embodiments, injector 12 has a second end 30 containing one or a plurality of apertures 36 through which a medicament is sprayed towards the SPG.

In some embodiments, injector 12 is slidably received in an introducer 18, as described above, and the method further includes (c) engaging introducer 18 with a nostril of the subject, such that a portion of the subject's nose is lifted upon engagement with introducer 18; and (d) sliding injector 12 from a storage position to an engaging position after introducer 18 is engaged with the nostril. As described above, the engaging position of injector 12 is situated medial and/or posterior and/or inferior to the SPG—medial and/or inferior in some embodiments, and medial, inferior, and posterior in other embodiments. In some embodiments, the medicament is provided in a container 14 connected to and in communication with injector 12, as described above, and the method further includes (e) squeezing container 14 containing the medicament in order to spray the medicament towards the SPG.

In some embodiments, the method includes pushing introducer 18 snugly and comfortably within a nostril to lift the tip of the subject's nose before positioning the nozzle 28 of injector 12 in proximity to the SPG, sliding tubular section 24 of injector 12 through passageway 48 in introducer 18, and/or sliding tubular section 24 of injector 12 on a track 52 of handle 20. This method for transnasally delivering a medicament will be understood by those of skill in the art with reference to FIGS. 1, 3, and 4 by way of anatomic reference, as well as the other figures showing device embodiments, elements of each of which can be combined and/or interchanged with each other, where those of skill in the art will readily appreciate the device construction and variants as well as the methods of delivery with reference to the present disclosure.

FIGS. 10-12B show elements of another device embodiment 254, which assembles in substantially the same manner as the device 54 shown in FIGS. 6-9, and which device 254 includes an injector 256 (including a hub 266) and an introducer 262, and which may also include (when assembled for use in delivering medicament) a medicament container embodied as a syringe 214 (that is engageable with the injector and partially receivable within the introducer). As illustrated, embodiments of the device may include a novel connector interface that provides locking functionality to provide an effectively fluid-patent engagement of the syringe 214 with the hub 266 of the injector 212. The locking engagement may provide for ensuring single-use functionality of the device (which may provide hygienic and other safety advantages).

The introducer 262 is illustrated with reference to FIGS. 10-10G, and may also be understood with reference to the structure and function described above regarding FIGS. 6-9. The introducer 262 includes an elongate generally cylindrical body wall defining a housing 270, which surrounds a lumen 271. The lumen 271 includes at least two longitudinal channels 272a, 272b parallel to each other, each channel forming a depressed track along a lumen-facing body wall surface. The longitudinal channels 272a, 272b merge to form a single channel 272 near the proximal end of the introducer 262. As shown in FIGS. 10E-10G, the channels 272, 272a, 272b may form (respectively) a goalpost shaped, a Y-shaped, or a U shaped configuration. This channel is configured to slidingly receive the stop-bar 268 of the injector hub 266, which is embodied as a channel-engaging lateral projection near the proximal injector end (as shown in FIGS. 11A-11B).

FIG. 10 shows a bottom perspective view of the introducer 262. FIG. 10A shows an external side view thereof. FIG. 10B shows a longitudinal section view along line 10B-10B of FIG. 10A, and FIG. 10C shows a transverse section view along line 10C-10C of FIG. 10D. One configuration of the channels 272, 272a, 272b is shown in FIGS. 10B-10C, and another in FIG. 10D. In particular, FIG. 10C illustrates the radial angle relative to the central longitudinal axis at which each of the channels 272a, 272b extends along a more distal length of the introducer body 270. The radial orientation of the stop bar 268 in each of the channels 272a, 272b when the stop bar 268 is distally advanced in the channel (such that the injector distal end 260 is extended out of the introducer 270 (in the same manner as shown in FIG. 8) provides for user-selectable orientation of the injector side aperture 236 toward the SPG region from each of the subject's right and left nostrils while preventing radial rotation of the injector 256 during the time it is extended into the subject's nostril.

FIG. 11B shows an inverted longitudinal section view (taken along line 11B-11B of FIG. 11), with this inverted orientation provided to show how the hub would align with and engage into the introducer 262 shown in FIGS. 10-10D. As shown in the magnified distal section detail of FIG. 11B, the side aperture 236 near the distal injector end 260 preferably is coplanar with a longitudinal axis (whether straight or curved) of the injector 256 and is oriented at a non-perpendicular angle relative to that axis such that the spray proceeding out of the aperture 236 is directed somewhat proximally and upward to target the SPG region along a spray path in the manner described above. In one embodiment, the aperture 236 may have a diameter of about 0.01 inches (about 0.25 mm) and be oriented at an angle between about 30° and about 60°, preferably about 45°. This orientation preferably provides an optimum spray path access to the SPG region in the manner described above with reference to FIG. 4.

The injector 256 with its hub 266 is illustrated in FIGS. 11-11B. The hub 256 is generally cylindrical with a proximal luer lock construction that may be made to comply with ISO standards 594-1 and 594-2. Its distal end region is configured to slidingly engage into the introducer lumen 271, with the stop bar 268 slidingly engaged into the channels 272 (and, upon actuation, a selected one of 272a or 272b). The stop bar 268 includes a weakened distal region 268a that is configured to fail and allow the stop bar to bend over and/or break off when subjected to a predetermined lateral force by rotation of the hub when the stop bar is engaged into a channel. The predetermined force preferably corresponds to a force required to overcome and disengage the connector interface described below (e.g., the same as or less than the rotational force required to overcome the lock between the syringe and the injector hub effected by tooth/notch and luer lock engagement, such that connecting then disconnecting a syringe from the hub will limit its effective use to a single-use). Delivery devices of the present disclosure and kits including them may be available under the trade name Tx360° from Tian Medical (Lombard, Ill.).

FIGS. 12-12B show a syringe assembly 214, configured to participate in a connector interface with the hub 266. FIG. 12 shows a disassembled perspective view of the plunger and barrel of the syringe 214. The syringe 214 may include one or more features providing for single-use functionality. As shown in FIGS. 12A-12B, the barrel 282 includes a proximal-end longitudinal inner track 283 that engages/receives opposing laterally-protruding fins 287 of a locking plunger 286 to provide for non-rotary longitudinal plunger movement within the barrel 282. The plunger 286 also includes opposed laterally extending locking flanges 285 that engage into a pair of opposed flange-receiving windows 284 in the barrel 282 when the plunger 286 is fully advanced into the barrel. This prevents withdrawal of the plunger 286 from the barrel 282 as one means of promoting single-use-only of the device. A spacer 289 may be provided to clip around the base of the plunger 286 and prevent inadvertent flange/window locking before the device is used.

With reference to FIGS. 12-12B, the distal end 290 of the syringe barrel 282 may be constructed to cooperate as part of a connector interface. It may be generally cylindrical with a proximal luer lock construction that may be made to comply with ISO standards 594-1 and 594-2. Described differently, it may be constructed to include a first cylindrical female portion 291 disposed coaxially around a first cylindrical male engaging portion 292, and a first engaging end defined by corresponding (although not necessarily coplanar) termini of the first cylindrical male portion 292 and the first cylindrical female portion 291, where the engaging end is the distal barrel end.

The luer lock portion of the proximal end of the hub 266 may be constructed to comply with ISO standards 594-1 and 594-2. Stated differently, it may include a second cylindrical female portion 266a (of the hub) that engagingly receives therein the first male portion 292 of the syringe. The second cylindrical female portion 266a is constructed as a lumen defined by a second cylindrical male portion 266b that engages into the first female portion 291. A second engaging end (that is, the engaging end of the hub 266) is defined by the co-terminus of the second cylindrical male portion and the second cylindrical female portion.

The first cylindrical female portion 291 includes a helically-threaded surface that engagingly receives/interfaces with the externally-protruding tabs 266c of the second male portion 266b (which tabs may be embodied as at least one tab, one or more lugs, or threads). Complete rotational engagement of the tabs 266c with the threaded surface of the first female portion 291 corresponds with full engagement of the first male portion with the second female portion to form a fluid-patent connection. This may be enhanced when the first male engaging portion includes a tapered configuration including a smaller outer diameter near the engaging end and a larger outer diameter longitudinally spaced from the engaging end, and where the larger outer diameter engages an inner diameter of the second female portion to form at least part of the effective fluid-patent seal between the first and second connector elements.

A locking functionality of the connector interface may be provided by a tooth-notch engagement between the injector hub of the introducer assembly and the distal barrel end of the syringe. Those of skill in the art will appreciate that the connector interface described here may be used in a variety of other settings, including non-medical devices and assemblies. Fluid-patent connections using a luer-lock-type construction and the presently-disclosed connection interface may readily be applied in the aerospace, automotive, and other industries. In particular, those of skill in the art will appreciate the usefulness and applicability of a fluid-patent connection interface that provides secure engagement and that also essentially provides for one-time use (where one or both elements of the connector interface will be damaged by disengagement after a complete engagement, thereby limiting re-use). Such single-use functionality will have readily-appreciated applicability in hygienic settings, as well as in other environments where there may be reasons for avoiding re-use such as potential food/liquid transport contamination, a need to provide visible indicia that a connection has been disengaged/tampered with, or other uses that will be appreciated by those having skill in the mechanical and related arts.

The hub 266 includes a plurality of teeth 269 extending generally longitudinally proximally along the outer surface of the second male portion 266b, proximal of the stop bar 268. The distal end of the syringe barrel 282 includes a corresponding plurality of notches 281. FIG. 12B shows the plunger 280 and a magnified (relative to the plunger) detail view of the barrel 282 (with the proximal portion shown as a longitudinal section). As shown in FIG. 12B, each notch 281 preferably is generally contoured as a right triangle with a first face 281a oriented at an acute angle relative to a plane defined by the barrel terminus and a second face 281b substantially perpendicular to the that plane.

Those of skill in the art will understand that, when the luer lock male and female components are fully rotationally engaged, the teeth 269 will engage the notches 281. As the syringe barrel 282 is rotatably engaged to the hub 266 by engagement of the tabs 266c into the threaded hub surface 291, the teeth 269 will press against the barrel's terminal surface plane until clicking past the second notch face 281b into the notch 281 and—as the threaded connection is further engaged—the teeth 269 will ride up the second notch face 281b in a manner biasing the hub away from the barrel and forcing the tabs/threads into tighter engagement.

The components all preferably are dimensioned so that complete engagement therebetween occurs at this point or form a locked relationship (engaged in a manner that requires damage to the longitudinal teeth and/or notches in order to reverse-rotate and disengage them from each other). In one preferred embodiment, the barrel and/or the teeth include a polymer construction (e.g., a polycarbonate) such that counter-rotation to disengage the pieces will bring the tooth up against the second notch face 281a and stop its progress unless over-forced sufficiently to damage the teeth and/or notch. In other embodiments, one or more components may include metal construction that would require even greater force to overcome the locking engagement. FIG. 13A shows an injector embodiment 266 of FIGS. 11-11B engaged into an introducer 262. FIG. 13B shows the injector 266 in an engaged/actuated state where its distal-most end extends out of the introducer to a position configured for medicament delivery to the SPG, and where the barrel of a syringe 282 engaged to an injector hub is received almost entirely within the body of the introducer 262 and the syringe plunger is shown as fully depressed (e.g., as if the syringe has been evacuated to deliver its entire contents).

It should be appreciated that the presently described embodiments are not limiting upon the uses of the locking mechanism described here. Specifically, by way of example, the tooth/notch locking mechanism described here may be implemented in other (e.g., non-medical) devices. For example, fluid-flow couplings in industrial equipment may be constructed with traditional luer-lock components and the novel outer locking structure presented herein. Those of skill in the mechanical arts will appreciate from the present disclosure (including the drawings) that the inventive tooth/notch locking system allows a user to rotatably "lock closed/engaged" the luer-lock components. Depending upon the materials used, counter-rotation to unlock those components preferably will either not be possible, or will be sufficiently destructive to the components so as to render the connector assembly effectively a single-use locking mechanism. For example, providing generally rigid stainless steel for both the teeth and the notches will allow a single-use (e.g., substantially permanent) locking, or one time locking, structure, while using a deformable or breakable polymer will do the same. For example, once locked, the mechanism cannot be unlocked without modifying or breaking it. The phrase "luer-lock" and components or elements thereof will readily be understood by those of skill in the mechanical arts with reference to the state of the art, to ISO 594 standards, although the present claims are not limited to a 6° taper for inner connections, as those of skill in the art will readily adapt the fitting components in special applications to other angles when needed.

Those having skills in the mechanical arts will appreciate from the present disclosure the novelty and usefulness of a luer-lock-type connector, applicable in a variety of medical, industrial, and other settings where a fluid-patent or otherwise secure, one-time lockable connection is desirable. Accordingly, in one aspect, embodiments presently disclosed may include a luer-lock connector interface that includes a first luer lock element with a cylindrical end including a plurality of asymmetrical notches where each of the notches includes a first face at an acute angle relative to a plane defined by the cylinder end and a second face at substantially a perpendicular angle relative to said plane; a second luer-lock element including a plurality of teeth that engage the notches and prevent disengaging counter-rotation of the second luer-lock element from the first luer-lock element after a complete engagement therebetween.

All manner of medicaments suitable for introduction at or in the vicinity of the SPG are contemplated for use in accordance with the present teachings. The physical state of the medicament includes but is not limited to liquids, solids, semi-solids, suspensions, powders, pastes, gels, and the like, and combinations thereof. In some embodiments, the medicament is provided in an at least partially liquid form. In preferred embodiments of the present disclosure, the medicament contains the first pharmaceutical agent (for BBB permeabilization enhancement via the SPG, e.g., a cholinesterase inhibitor) in a first aqueous solution or suspension, which may be a saline aqueous solution or suspension, and the second pharmaceutical agent (for delivery into the brain/CNS tissue via the SPG) in a standard dosage form for said agent, where a preferred dosage form may be intravenous in order to maximize the effectiveness of the permeabilized BBB while minimizing the amount of the second agent needed to be effective (thereby reducing subject exposure and cost). A method for treating a disorder comprising one or more of Lewy body dementia, vascular dementia, seizure, stroke, Parkinson's Disease, Alzheimer's Disease, multiple sclerosis, headache, Amyotrophic Lateral Sclerosis, Adrenoleukodystrophy (ALD) (including Childhood Cerebral Adrenoleukodystrophy (CCALD)), vascular dementia, idiopathic senile dementia, multiple sclerosis, benign and cancerous brain tumors, schizophrenia, major depression, multiple personality disorder, bipolar disorder, and/or any other physiological or psychiatric disorder known to be responsive to treatment with a CNS-acting pharmaceutical agent, said method comprising steps of:

transnasally administering to or immediately adjacent the sphenopalatine ganglion a first pharmaceutical agent that effectively enhances permeability of the blood-brain barrier; and thereafter administering a second pharmaceutical agent with known efficacious value for action upon central nervous system tissue, where each pharmaceutical agent should be understood to include pharmaceutical salts and the standard variants of those particular agents known in the medical and pharmaceutical arts, and where the step of administering the second pharmaceutical agent may be done transnasally in the same manner of targeted delivery to the SPG, or that step of administering may be done in whatever mode/method the second pharmaceutical agent is normally delivered (including at least intravenously which may be optimal for many such pharmaceutical agents, but which may also include—additionally or instead—orally, intramuscularly, via inhalation, via perfusion, transdermally, or by any other delivery method known, used, and/or developed in the art).

In some embodiments, the medicament used in accordance with the present teachings is provided in a container 14 (shown in FIGS. 1, 3, 4) as a pressured or aerosolized mixture, or may be loaded into a syringe such as the syringe embodiment shown in FIGS. 12-12B, or another syringe, the barrel of which will be received into the lumen 271 of the housing 270 when the injector 256 is advanced distally (e.g., as shown in the transition from FIGS. 6 and 7 to FIG. 8). The medicament optionally contains preservatives, a liquid carrier, and/or other inert ingredients and additives as will be readily appreciated by those of ordinary skill in the art.

The amount of medicament delivered in accordance with the present teachings can be readily determined by one of ordinary skill in the art and will vary according to factors such as the nature and/or concentration of the medicament, the subject's age, condition, and/or sensitivity to the medicament, and the like. In some embodiments, the dosage volume ranges from about 0.1 cc to about 1.0 cc, containing a therapeutically effective amount of the second pharmaceutical agent for delivery after permeabilization enhancement by the first pharmaceutical agent (e.g., a cholinesterase inhibitor or other agent such as insulin or another permeabilization-enhancer), if the second pharmaceutical agent is to be delivered transnasally to/via the SPG. The dosage amount of the second pharmaceutical agent, when delivered via other means may be determined without undue experimentation beginning with a standard dosage amount, with an effective dose expected to be less after the presently-described BBB permeabilization. In a preferred method of treatment, a fraction of the standard dosage may be used and effective, particularly when administered intravenously or in another manner that introduces the second pharmaceutical agent or its effective metabolite into the subject's bloodstream within the timeframe of increased BBB permeability. For example, the BBB permeabilization steps may be done shortly before intravenous introduction of the second pharmaceutical agent. As another example, the BBB permeabilization steps may be done after an oral dosage administration or other administration of the second pharmaceutical agent, timed to permeabilize the BBB in a timeframe corresponding to known and preferably increased levels in the subject's blood of the second pharmaceutical agent. Those of skill in the relevant arts will recognize and understand that this description refers to and includes the presence in the subject's blood of the effective metabolites and/or other products from the second pharmaceutical agent.

Methods and devices described herein are contemplated for use in the treatment of all manner of conditions for which the introduction of a medicament superiorly and/or laterally and/or anteriorly towards the SPG of a subject is desirable. For example, the present methods may also be effective for preventing or at least reducing the incidence and/or severity of symptoms of seizure, stroke, Parkinson's Disease, Alzheimer's Disease, multiple sclerosis, vascular dementia, idiopathic senile dementia, multiple sclerosis, benign and cancerous brain tumors, headache, Amyotrophic Lateral Sclerosis, Adrenoleukodystrophy (ALD) (including Childhood Cerebral Adrenoleukodystrophy (CCALD)), schizophrenia, and bipolar disorder for treating particular conditions and/or disorders whether or not specifically identified herein.

Topical administrations of a medicament to human tissue for the systemic delivery of a pharmaceutically active agent typically include the use of transdermal and/or transmucosal pastes, creams, liquids, solids, semisolids, and the like. However, systemic delivery of pharmaceutically active agents by topical administration is hampered by the difficulty of diffusing an agent through the tissue to which the agent is applied in order to reach blood vessels, whereby the agent can then be absorbed for systemic delivery, and the same or similar challenges may apply where the medicament is absorbed internally via peroral dosage/ingestion. Thus, to address this difficulty, the methods and devices described herein may be invoked to achieve increased permeability of the blood brain barrier in the administration of any medicament. In view of the surprisingly effective clinical results described below during animal testing, the transnasal delivery of an SPG-targeted dosage of a first pharmaceutical agent before dosage of a CNS-active second pharmaceutical agent is expected to reduce the likelihood and incidence of side effects, particularly those associated with higher dosages and/or with gastro-intestinal metabolism of peroral administration. Stated differently, in view of the BBB permeabilization, it is expected that (during the time window of transnasally-administered-AChE-inhibitor enhanced BBB permeability) the administration of a CNS-acting second pharmaceutical agent whether in its standard dosage form and/or also administered transnasally to the SPG will be effective at a lower dosage than that second pharmaceutical agent would be without the BBB permeabilization of the present disclosure. This lower effective dosage is predicted and expected to reduce costs, to reduce the incidence and severity of dosage-related side effects, and to improve subject outcomes.

The term "kit" refers to an assembly of materials that are used in performing a method in accordance with the present teachings. Such kits can include one or a plurality of devices and/or components thereof, including but not limited to the representative devices described above, and may further include one or more medicaments to be used therewith.

In some embodiments, a kit includes an injector and/or an introducer, each of which is configured for engagement with a left-side nostril of the subject. In some embodiments, a kit includes an injector and/or an introducer configured for engagement with a right-side nostril of the subject. In some embodiments, a kit includes an injector and an introducer configured for engagement with a left-side nostril of the subject, as well as an injector and an introducer configured for engagement with a right-side nostril of the subject. Optionally, an interchangeable handle can also be provided for connection to either of the right-handed and left-handed introducers. In other embodiments, the handle itself exhibits handedness, and separate handles can be provided for each of the right-handed introducer and the left-handed introducer, where—in any event—the medicament may be delivered via one or both nostrils (e.g., one-half each, or some other fractional division resulting in a whole dose).

In some embodiments, the device will be provided in a fully assembled state, while in other embodiments assembly of the device will be required. In some embodiments, the device provided in the kit includes a delivery tube having a curved portion at one of its ends configured for insertion into a subject's nostril, wherein the delivery tube is housed within a substantially cylindrical (e.g., pen- or cigar-shaped) housing, such as the type described above. In some embodiments, one or a plurality of the components of the device is disposable and, optionally, biodegradable.

The medicament may be provided in a kit as a single reagent or a plurality of reagents. Representative medicaments for use in accordance with the present teachings include but are not limited to those described above. The medicaments may be provided in packaged combination in the same or in separate containers, depending on their cross-reactivities and stabilities, and in liquid or in lyophilized form. The amounts and proportions of any reagents provided in the kit may be selected so as to provide optimum results for a particular application. In other embodiments, the device may be provided in the kit, and the medicament may be obtained separately. For example, a peroral tablet may be obtained, crushed, and dissolved/suspended into water that preferably is sterile and/or otherwise appropriate for pharmaceutical use in delivering medicament transnasally. The water may include or may have added other components to provide pH buffering, salinity, or other desired qualities.

Kits in accordance with the present teachings may also be supplied with other items known in the art and/or which may be desirable from a commercial and user standpoint, such as empty syringes, tubing, gauze, pads, disinfectant solution, cleaning solutions, instructions for performing a transnasal delivery of medicament, and/or for assembling, using, and/or cleaning the device, and the like, and combinations thereof.

In some embodiments, instructions may be affixed to one or more components of the device and/or the containers (e.g., vials), or to a larger container in which one or more components of the kit are packaged for shipping. The instructions may also be provided as a separate insert, termed the package insert. Instructional materials provided with kits may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail.

In use, the optional handle 20 of the devices 10 described herein can be pushed towards the subject's face until introducer 18 snugly and comfortably engages and fits within the subject's nostril to lift the flat tip of the subject's nose to point superiorly and slightly posteriorly. Thereafter, the injector 12 can be pushed posteriorly towards the subject's nose to slide tubular section 24 and nozzle 28 rearwardly until nozzle 28 is located medially and/or posteriorly and/or inferiorly to the SPG—medially and/or inferiorly in some embodiments, and medially, inferiorly, and posteriorly in other embodiments (where the nozzle preferably travels below and immediately adjacent the middle turbinate). Thereafter, a medicament such as a mixture, solution, emulsion, or suspension including each respective pharmaceutical agent can be injected and sprayed through apertures 36 of nozzle 28 upwardly and/or laterally and/or anteriorly towards and about the SPG to treat a subject—where the spray is directed toward the SPG laterally and/or upwardly in some embodiments, and laterally, upwardly, and anteriorly in other embodiments.

The following examples illustrate features of the devices and methods described herein and are provided solely by way of illustration. They are not intended to limit the scope of the appended claims or their equivalents.

Example 1

The devices and methods described above are expected to successfully be applied to the treatment of human subjects for treatment of one or more conditions, where a device and method as described above is used to deliver 1 mg of rivastigmine dissolved in less than 1 mL of aqueous solution transnasally to the SPG (preferably with about ½ via the right nostril and about ½ via the left nostril). Within about 1 minute to about 60 minutes and preferably within about 30 minutes, a second pharmaceutical agent will also be delivered, where the second pharmaceutical agent is a CNS-effective therapeutic agent known or at least predicted within standard practices by the physician to be effective in treating one or more subject ailments, including expressly those identified above.

In addition to and including cholinesterase inhibitors listed elsewhere, reversible competitive and/or noncompetitive inhibitors of cholinesterase may include carbamates (e.g., physostigmine, neostigmine, pyridostigmine, ambenonium, demecarium, rivastigmine), phenanthrene derivatives (e.g., galantamine), caffeine (as a noncompetitive inhibitor and also as an adenosine receptor antagonist), piperidines (e.g., donepezil), tacrine (also known as tetrahydroaminoacridine (THA')), edrophonium, huperzine A, ladostigil, ungeremine, and lactucopicrin, each of which may be included in certain embodiments for cholinesterase inhibition to help permeabilize the blood-brain barrier, although certain of these may be more preferred or less preferred for best efficacy and any combination thereof may be useful. The neurotoxic effects of irreversible and semi-irreversible cholinesterase inhibitors make them far less preferable, although it may be within the skill in the art to use such, (for example at a very low dosage, with co-delivered and/or later-delivered materials that would reverse the inhibition effects that are not reversible within the normal function/cellular interaction of those materials). Although not listed in every instance in the present disclosure, it is contemplated that the presently-described methods of treatment will be effective in treating and/or will enhance the efficacy in existing pharmaceutical treatments of central nervous system ailments, and brain disorders in particular, including at least bipolar disorder, catalepsy, epilepsy including absence epilepsy and other epileptic seizures, encephalitis, meningitis, migraine, tropical spastic paraparesis, arachnoid cysts, Huntington's Disease, Alzheimer's Disease, Parkinson's Disease, attention deficit/hyperactivity disorder (ADHD), attention deficit disorder (ADD), sleep disorders receptive to CNS-active pharmaceutical agents, locked-in syndrome, Tourette's Syndrome, forms of autism responsive to pharmaceutical agents, addiction to and/or withdrawal from opioids and/or prescription drugs, and/or multiple sclerosis, including whether those or other ailments are congenital and/or associated with trauma, infection, degeneration due to age and/or disease, benign or cancerous tumors, stroke, autoimmune disorder, and/or structural anomalies of cells, tissues, or other body elements.

Example 2

Male Sprague-Dawley rats (Harlan, Indianapolis, Ind.) weighing 300-350 g were allowed to acclimate for at least 4 days prior to experimentation. Rats were housed 2 per cage in a room with controlled light (6:00 a.m. to 6:00 p.m.), humidity (50±10%) and temperature (23±1° C.). Animal care and use for experimental procedures was approved by and in accordance with the guidelines of the Midwestern University Institutional Animal Care and Use Committee (IACUC).

All drugs/solutions were freshly prepared on the day of administration using sterile saline (0.9% NaCl, Hospira, Inc., Lake Forest, Ill.). Urethane (ethyl carbamate, Sigma-Aldrich, St. Louis, Mo.) was administered intraperitoneally (IP) at a dose of 1.5 g/kg. Neostigmine (0.4 mg/kg; Sigma-Aldrich) and rivastigmine (1, 2 and 4 mg/kg; Sigma-Aldrich) were administered topically to the SPG via intranasal cannula at a max volume of 10>1. Evans blue (5 mL/kg) was administered intravenously (IV) via left femoral vein cannula.

Two studies were designed for this project, using a total of 42 rats. Study I was designed to determine the effects of intranasal application of 2 different acetylcholinesterase inhibitors (neostigmine and rivastigmine) to the SPG on cardiovascular parameters and BBB permeability. Based on the results of the initial study, Study II investigated the dosing effect of rivastigmine application to the SPG on cardiovascular parameters, BBB permeability and cerebral blood flow. Animals for Study I were divided into three groups (n=6/group): Group 1: Saline; Group 2: Rivastigmine 1 mg/kg; and Group 3: Neostigmine 0.4 mg/kg. Animals for Study II were divided into four groups (n=6/group): Group 1: Saline; Group 2: Rivastigmine 1 mg/kg; Group 3: Rivastigmine 2 mg/kg; and Group 4: Rivastigmine 4 mg/kg.

Rats were anesthetized with urethane (1.5 g/kg, IP) and immobilized on a surgical board equipped with a controlled heating pad. Core temperature, measured via rectal probe, was maintained at 37±1° C. In order to maintain blood $pO_2$, $pCO_2$ and pH, and to avoid the effect of respiration on blood pressure (BP) and heart rate (HR), animals were kept on artificial respiration via an endotracheal cannula connected to a rodent ventilator (Model 683, Harvard Apparatus, Inc., Holliston, Mass.). The left femoral artery was cannulated with pressure transducer SPR-320 (Millar Instruments) for measurement of HR and mean arterial pressure (MAP). The transducer was connected to a ML221 bridge amplifier (AD Instruments, Mountain View, Calif.) through an AEC-10C connector and the signals were acquired (1000 S-1) using the PowerLab 16/30 data acquisition system (AD Instruments). The left femoral vein was cannulated with PESO tubing (Clay Adams, Parsippany, N.J.) for administration of Evans blue dye (5 mL/kg). The right nare was cannulated with PE10 tubing to a depth of ~25 mm or until the tip touches the SPG for administration of the acetylcholinesterase inhibitor. The placement of tubing was confirmed to be in the proximity of SPG in each animal by autopsy at the end of the experiment in order to be included in the study.

Animals anesthetized with urethane were secured into a stereotactic apparatus (David Kopf Instruments, Tujunga, Calif.) and a midline incision was made on their scalp. The skull was slowly thinned using a dremel, working in 30 second periods to minimize heat caused by friction. Cerebral blood flow was measured using Laser Speckle Contrast Analysis (LASCA) technology with a PeriCam PSI HR system (Perimed, Inc., Ardmore, Pa.), captured in real time and analyzed using PIMSoft software (Perimed).

At the conclusion of the experiment, the rat was perfused transcardially with 300-400 mL of ice cold saline and the brain was removed. The brain was then placed in 2 mL formamide (Sigma-Aldrich) and incubated at room temperature for 48 hours. The supernatant was removed and absorbance was measured at 625 nm using a spectrophotometer (Spectronic Instruments, Rochester, N.Y.). The tissue was then dried in an oven at 95° C. for 5 days. Evans blue concentration was calculated as microgram of dye per milligram of dry weight brain tissue as based on the standard curve.

GraphPad Instat 2.00 was used to conduct a power analysis. Power analysis indicated that a sample size of 6 per group was sufficient to achieve a power of 80% ($\beta=0.8$) when the level of significance was set to 0.05 ($\alpha=0.05$). Data are presented as mean±SEM. The significance of differences for mean arterial pressure, heart rate and cerebral blood flow was estimated by 2-way analysis of variance followed by Tukey's post hoc test. One-way analysis of variance followed by Tukey's post hoc test was used to estimate significance for BBB permeability. A P value of less than 0.05 was considered significant. The statistical analysis was processed with GraphPad Prism 6.05 (GraphPad, San Diego, Calif.).

Figure 14A:
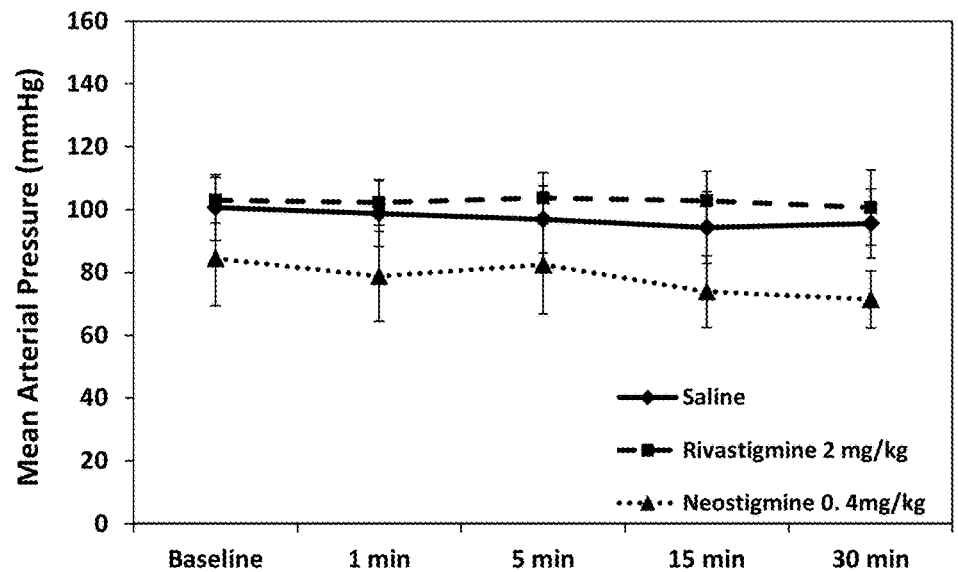
FIG. 14A shows the effect of intranasal topical application of saline, rivastigmine (2 mg/kg) and neostigmine (0.4 mg/kg) on mean arterial pressure.
Figure 14B:
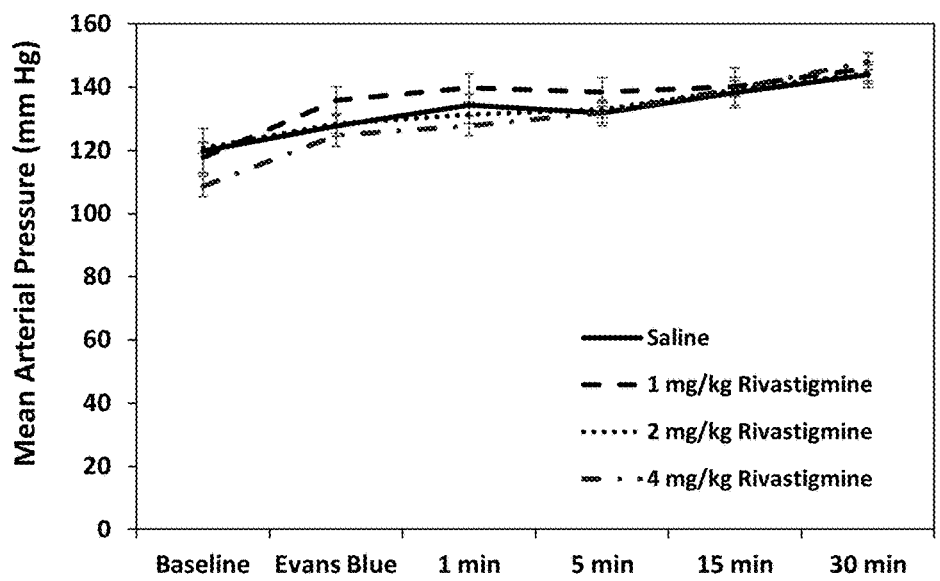
FIG. 14B shows the dose-dependent effect of rivastigmine (1, 2 and 4 mg/kg) on mean arterial pressure. Values are presented as mean±SEM. N=6/group.

Mean arterial pressure did not significantly alter following administration of either saline or rivastigmine (1, 2 or 4 mg/kg) to the SPG via intranasal cannula. Application of 0.4 mg/kg neostigmine did show a slight decrease in mean arterial pressure at 15 and 30 min postadministration, but the reduction in MAP was not significant (FIG. 14).

Figure 15A:
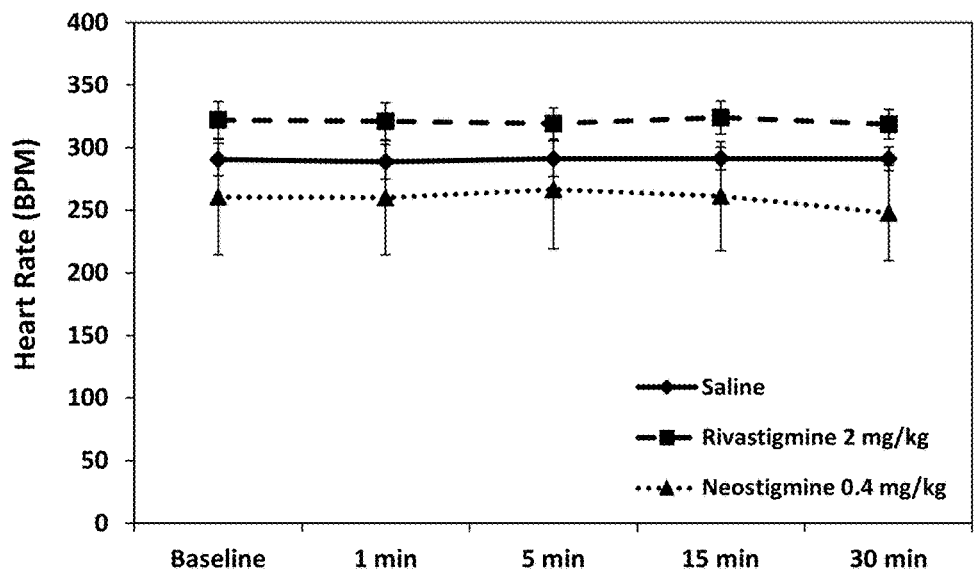
FIG. 15A shows the effect of intranasal topical of saline, rivastigmine (2 mg/kg) and neostigmine (0.4 mg/kg) on heart rate.
Figure 15B:
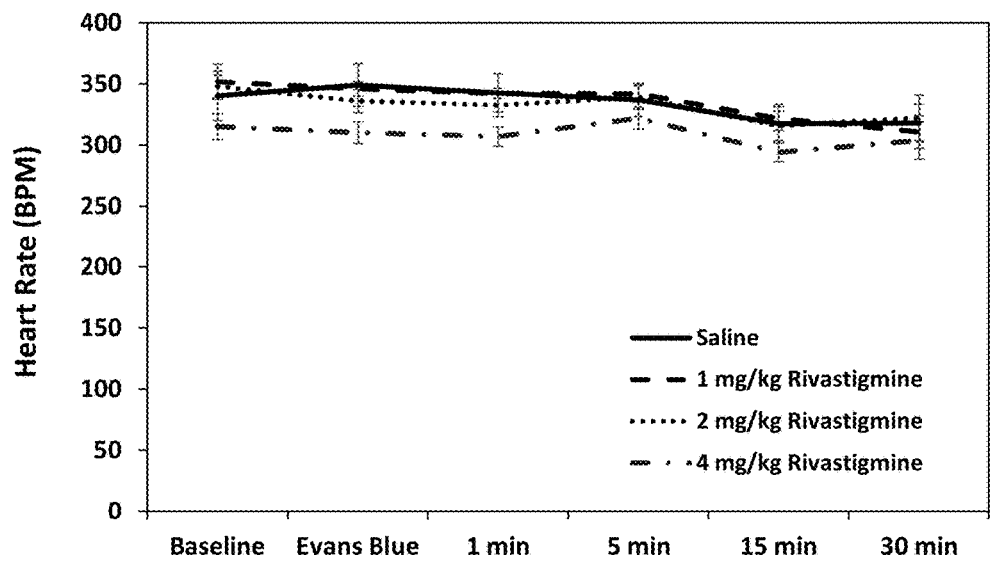
FIG. 15B shows the dose-dependent effect of rivastigmine (1, 2 and 4 mg/kg) on heart rate. Values are presented as mean±SEM. N=6/group.

Heart rate did not significantly vary with the administration of either saline or rivastigmine (1, 2 or 4 mg/kg) to the SPG via intranasal cannula. As with MAP, the neostigmine group did show a slight decrease in heart rate over time, but the difference was not significant (FIG. 15).

Figure 16A:
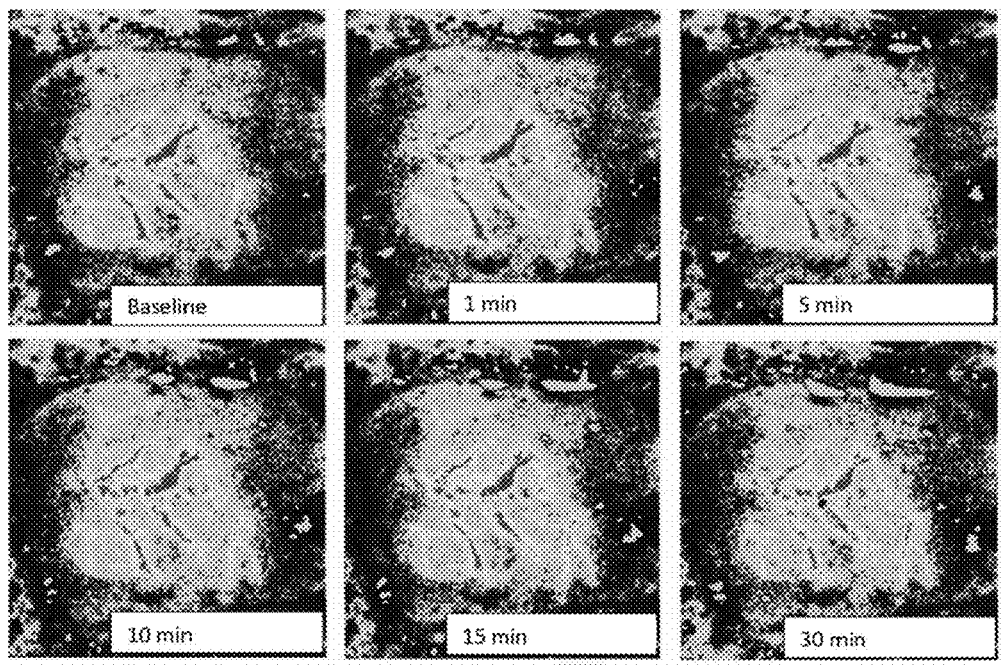
FIG. 16A shows representative images of the effect of rivastigmine (1 mg/kg) on cerebral blood flow using a PeriCam PSI HR system (Perimed).
Figure 16B:
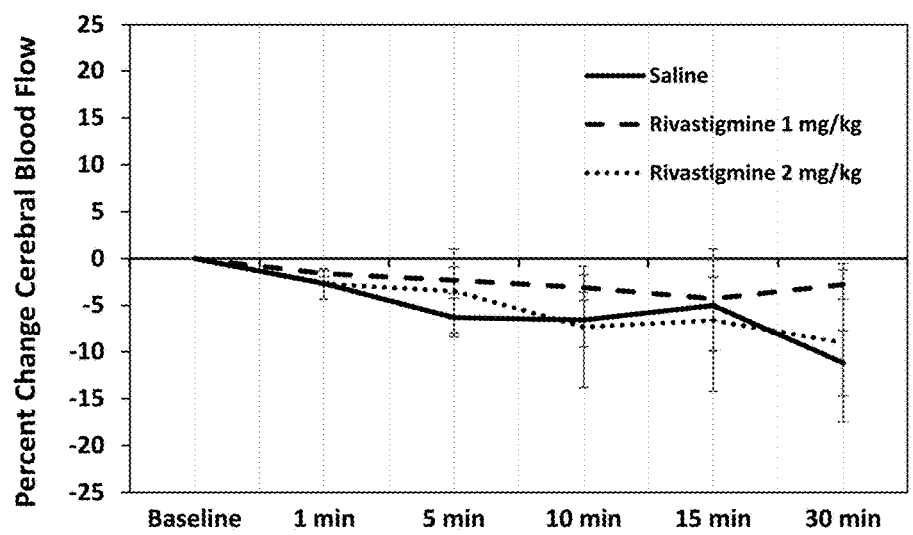
FIG. 16B shows the dose-dependent effect of rivastigmine (1 and 2 mg/kg) on percent change in cerebral blood flow. Values are presented as mean±SEM. N=6/group.

Cerebral blood flow remained relatively stable throughout the experiment. No significant differences were noted between saline or rivastigmine-treated animals (FIG. 16).

Figure 17A:
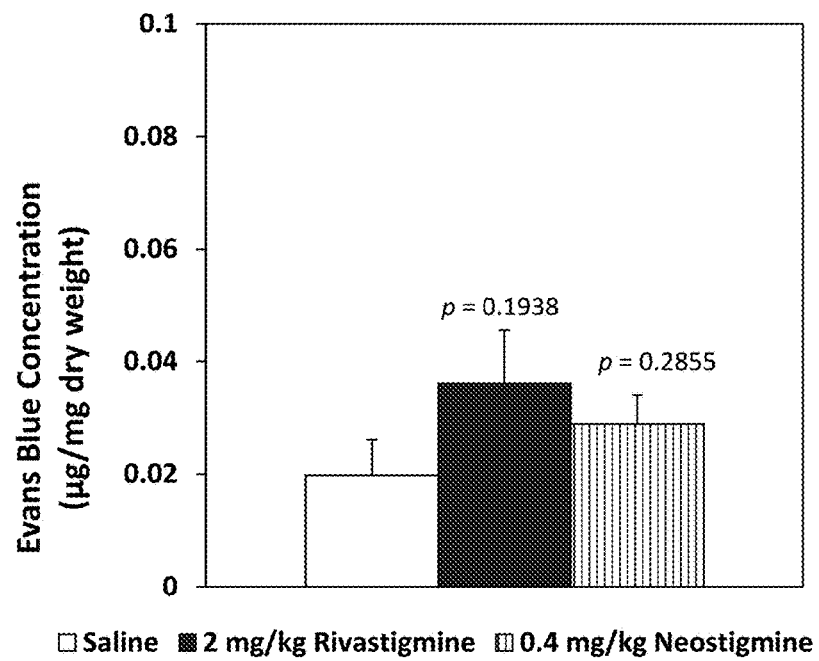
FIG. 17A shows the effect of intranasal topical application of saline, rivastigmine (2 mg/kg) and neostigmine (0.4 mg/kg) on BBB permeability as determined by Evans Blue concentration within the brain.
Figure 17B:
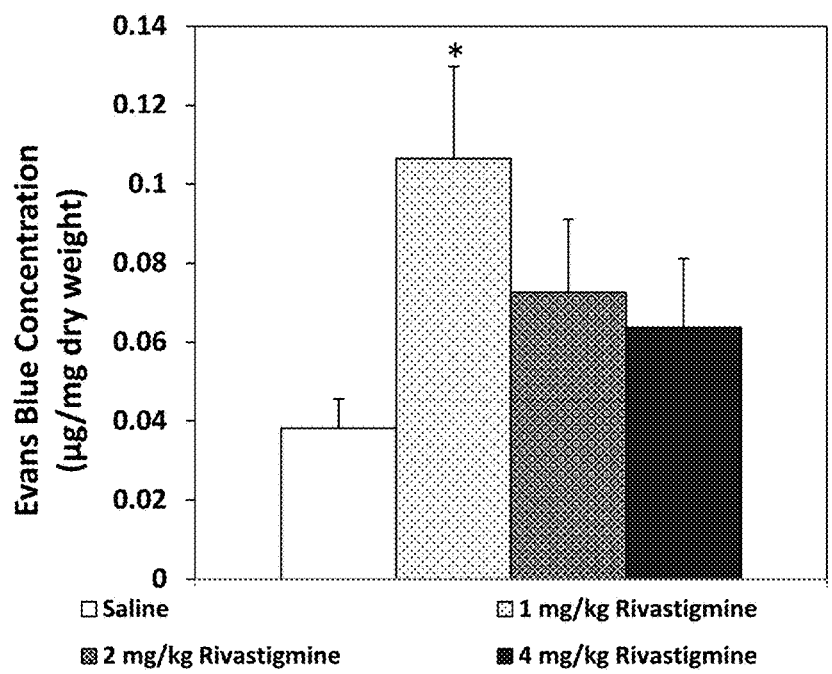
FIG. 17B shows the dose-dependent effect of rivastigmine (1, 2 and 4 mg/kg) on BBB permeability. Values are presented as mean±SEM. N=6/group. *P<0.05 vs. saline.

Evans blue is a high molecular weight permeability marker. Rivastigmine, which inhibits both butylchoinesterase and acetylcholinesterase, crosses the BBB, whereas neostigmine does not. In Study I, the 2 mg/kg dose of rivastigmine showed a slightly increased permeability of the BBB over neostigmine (FIG. 17). Subsequently, in Study II, an increase in BBB permeability was noted with 0.11±0.02>g Evans blue per mg dry brain weight in the 1 mg/kg rivastigmine group, which was significantly higher than saline (0.04±0.01>g/mg dry weight), 2 mg/kg rivastigmine (0.07±0.02>g/mg dry weight), and 4 mg/kg rivastigmine (0.06±0.02>g/mg dry weight).

Topical administration of rivastigmine to the SPG increased the concentration of Evans Blue dye in the CNS, thus indicating an increase in BBB permeability. A lower dose of rivastigmine produced more significant opening of the BBB compared to a higher dose. Without being bound by any theory, it is possible that an auto-regulatory system in the brain allows a smaller dose of rivastigmine to open the BBB, on the other hand, a higher dose reduces its efficacy possibility due to cerebral auto-regulation.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

What is claimed is:

1. A method for treating brain tissue of a human or other mammalian subject, the method comprising steps of:
   (a) transnasally administering to the subject a first pharmaceutical agent in an amount effective to increase blood-brain barrier permeability above an initial default permeability state to a second, more-permeable state for a dose-dependent limited time; and
   (b) thereafter, administering to the subject a second pharmaceutical agent in an amount that is therapeutically effective to measurably interact with brain tissue;
   wherein, the transnasal administration steps include targeted spraying from within a posterior portion of the nasal cavity directed laterally and superiorly toward the sphenopalatine ganglion such that a volume of the first pharmaceutical agent is delivered onto nasal mucosa immediately overlying the sphenopalatine ganglion.

2. The method of claim 1, wherein the first pharmaceutical agent is a cholinesterase inhibitor.

3. The method of claim 1, wherein the first pharmaceutical agent comprises one or more of galantamine, donepezil, huperzine, rivastigmine, tacrine, physostigmine, insulin, or a combination thereof.

4. The method of claim 1, wherein the second pharmaceutical agent comprises pharmaceutical agents known to have a therapeutic effect in central nervous system tissue.

5. The method of claim 1, where the first pharmaceutical agent comprises rivastigmine.

6. The method of claim 1, wherein the transnasal administration step includes using a delivery device that comprises:
   (a) an injector including a first end configured to remain outside a nasal passage of the subject and a second end configured for entry into the nasal passage of the subject, where the second end is configured for fluid communication with a syringe; and
   (b) an introducer configured for engagement partially into a nostril of the subject;
   where a distal portion of the injector includes a lateral-side aperture through which the first or the second pharmaceutical agent is to be sprayed.

7. The method of claim 6, wherein the introducer comprises a passageway that slidably receives the injector, and the passageway slidably receives within the introducer a barrel portion of a syringe when the syringe is attached to the injector and the injector is advanced distally out of the passageway, and
   wherein the injector lateral-side aperture is disposed at an acute angle relative to a central longitudinal axis of the introducer; and
   wherein the injector is moveable, relative to the introducer, between a storage position at least partially within the introducer and an engaging position where the injector extends from the introducer sufficiently to position the aperture within the subject's nasal cavity inferiorly, laterally, and/or posteriorly relative to the subject's sphenopalatine ganglion.

8. A kit for effecting the method of claim 6, said kit comprising a syringe, the introducer, and the injector.

9. The method of claim 6, further comprising steps of:
   (a) introducing the first pharmaceutical agent into a syringe;
   (b) attaching the syringe to the injector;
   (c) engaging a distal portion of the introducer partially into a nostril of the subject;
   (d) directing the syringe into the introducer in a manner distally advancing the injector through the distal portion of the introducer into a nostril of the subject so that the aperture is adjacent the sphenopalatine ganglion; and
   (e) actuating the syringe to effect the transnasal administration step by spraying the first pharmaceutical agent through the aperture.

10. The method of claim 9, where the aperture is advanced posteriorly below and past the middle turbinate and oriented toward the SPG of the subject.

11. The method of claim 9, further comprising steps of:
(a) introducing the second pharmaceutical agent into a syringe;
(b) attaching the syringe to an injector;
(c) engaging a distal portion of an introducer partially into a nostril of the subject;
(d) directing the syringe into the introducer in a manner distally advancing the injector through the distal portion of the introducer into a nostril of the subject so that the aperture is adjacent the sphenopalatine ganglion; and
(e) actuating the syringe to effect the transnasal administration step by spraying the second pharmaceutical agent through the aperture.

12. The method of claim 11, where the aperture is advanced posteriorly below and past the middle turbinate and oriented toward the SPG of the subject.

13. The method of claim 1, where the therapeutically effective amount of the second pharmaceutical agent is a therapeutically effective amount for interacting with brain tissue and treating a disorder comprising one or more of bipolar disorder, catalepsy, epilepsy including absence epilepsy and other epileptic seizures, encephalitis, meningitis, migraine, tropical spastic paraparesis, arachnoid cysts, Huntington's Disease, Parkinson's Disease, attention deficit/hyperactivity disorder (ADHD), attention deficit disorder (ADD), sleep disorders receptive to CNS-active pharmaceutical agents, locked-in syndrome, Tourette's Syndrome, forms of autism responsive to pharmaceutical agents, addiction to and/or withdrawal from opioids and/or prescription drugs, and/or multiple sclerosis, including whether those or other ailments are congenital and/or associated with trauma, infection, degeneration due to age and/or disease, benign or cancerous CNS tumors, autoimmune disorder, and/or structural anomalies of cells, tissues, or other body elements, Lewy body dementia, vascular dementia, seizure, stroke, Alzheimer's Disease, multiple sclerosis, headache, Amyotrophic Lateral Sclerosis, Adrenoleukodystrophy (ALD) (including Childhood Cerebral Adrenoleukodystrophy (CCALD)), idiopathic senile dementia, schizophrenia, major depression, multiple personality disorder, bipolar disorder, and/or any other physiological or psychiatric disorder known to be responsive to treatment with a brain tissue CNS acting pharmaceutical agent.

14. The method of claim 2, where the inhibitor comprises one or more of carbamates, phenanthrene derivatives, caffeine, piperidines, tacrine, edrophonium, huperzine A, ladostigil, ungeremine, lactucopicrin, or a combination thereof.

15. A method for treating brain tissue, said method comprising steps of:
(a) transnasally administering to or immediately adjacent the sphenopalatine ganglion a first pharmaceutical agent that effectively enhances permeability of the blood-brain barrier; and
(b) thereafter administering a second pharmaceutical agent with known efficacious action upon brain tissue.

16. A method for delivering a pharmaceutical agent to the brain comprising contacting a subject's sphenopalatine ganglion (SPG) with a cholinesterase inhibitor and administering a therapeutically effective dose of a pharmaceutical agent to the subject.

17. The method of claim 16, wherein the cholinesterase inhibitor comprises one or more of physostigmine, neostigmine, pyridostigmine, ambenonium, demecarium, rivastigmine, galantamine, caffeine, donepezil, tacrine, edrophonium, huperzine A, ladostigil, ungeremine, lactucopicrin, or a combination thereof.

18. The method of claim 16, wherein pharmaceutical agent comprises a CNS-acting pharmaceutical agent.

19. A method for permeabilizing a subject's blood brain barrier comprising contacting the subject's sphenopalatine ganglion (SPG) with a cholinesterase inhibitor.

20. The method of claim 19, wherein the cholinesterase inhibitor comprises one or more of physostigmine, neostigmine, pyridostigmine, ambenonium, demecarium, rivastigmine, galantamine, caffeine, donepezil, tacrine, edrophonium, huperzine A, ladostigil, ungeremine, lactucopicrin, or a combination thereof.

21. The method of claim 19, wherein the contacting is performed by transnasal administration.

22. The method of claim 21, wherein transnasal administration comprises using a delivery device that comprises:
(a) an injector including a first end configured to remain outside a nasal passage of the subject and a second end configured for entry into the nasal passage of the subject, where the second end is configured for fluid communication with a syringe; and
(b) an introducer configured for engagement partially into a nostril of the subject;
where a distal portion of the injector includes a lateral-side aperture through which the first or the second pharmaceutical agent is to be sprayed.

23. The method of claim 19, wherein a therapeutic pharmaceutical agent is co-administered to the subject.

24. The method of claim 23, wherein the therapeutic pharmaceutical agent comprises a CNS-acting pharmaceutical agent.

25. The method of claim 23, wherein the co-administration is oral, sublingual, topical, transdermal, ophthalmic, otic, nasal, rectal, vaginal, intramuscular, subcutaneous, intradermal, intravenous, intrathecal, epidural, or a combination thereof.

26. A method for treating brain tissue, the method comprising transnasally administering cholinesterase inhibitor to the subject's sphenopalatine ganglion (SPG) and co-administering a brain tissue acting pharmaceutical agent.

27. The method of claim 26, wherein the co-administration is oral, sublingual, topical, transdermal, ophthalmic, otic, nasal, rectal, vaginal, intramuscular, subcutaneous, intradermal, intravenous, intrathecal, epidural, or a combination thereof.

* * * * *

UNITED STATES PATENT AND TRADEMARK OFFICE
CERTIFICATE OF CORRECTION

PATENT NO.         : 10,039,736 B1
APPLICATION NO.    : 15/296069
DATED              : August 7, 2018
INVENTOR(S)        : Xia Page 1 of 1

It is certified that error appears in the above-identified patent and that said Letters Patent is hereby corrected as shown below:

In the Claims

Column 29, Claim 13, Line 47, please delete "CNS".

Signed and Sealed this
Thirtieth Day of October, 2018

Andrei Iancu
*Director of the United States Patent and Trademark Office*